(12) United States Patent
Walcott et al.

(10) Patent No.: US 6,760,621 B2
(45) Date of Patent: *Jul. 6, 2004

(54) METHOD FOR IMPROVING CARDIAC FUNCTION FOLLOWING DELIVERY OF A DEFIBRILLATION SHOCK

(75) Inventors: Gregory P. Walcott, Wilsonville, AL (US); Fred William Chapman, Newcastle, WA (US); Raymond E. Ideker, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 165 days.

This patent is subject to a terminal disclaimer.

(21) Appl. No.: 10/012,115

(22) Filed: Nov. 13, 2001

(65) Prior Publication Data

US 2002/0161407 A1 Oct. 31, 2002

Related U.S. Application Data

(63) Continuation-in-part of application No. 09/772,225, filed on Jan. 29, 2001, now Pat. No. 6,556,856.

(51) Int. Cl.[7] .................................................. A61N 1/39
(52) U.S. Cl. .......................................................... 607/6
(58) Field of Search .................................. 607/4–8, 14

(56) References Cited

U.S. PATENT DOCUMENTS

| 4,574,810 | A | * | 3/1986 | Lerman | |
|---|---|---|---|---|---|
| 5,292,338 | A | | 3/1994 | Bardy | 607/5 |
| 5,314,448 | A | | 5/1994 | Kroll et al. | |
| 5,593,428 | A | | 1/1997 | Jamshidi | 607/10 |
| 5,643,324 | A | | 7/1997 | Persson | 607/5 |
| 5,645,571 | A | | 7/1997 | Olson et al. | 607/5 |
| 5,700,281 | A | | 12/1997 | Brewer et al. | 607/5 |
| 5,735,876 | A | | 4/1998 | Kroll et al. | |
| 5,782,878 | A | | 7/1998 | Morgan et al. | 607/5 |
| 5,782,883 | A | | 7/1998 | Kroll et al. | |
| 5,824,017 | A | | 10/1998 | Sullivan et al. | 607/5 |
| 5,871,510 | A | | 2/1999 | Kroll et al. | |
| 5,902,323 | A | | 5/1999 | Brewer et al. | 607/5 |
| 5,968,080 | A | | 10/1999 | Brewer et al. | 607/8 |
| 5,978,703 | A | | 11/1999 | Kroll et al. | |
| 5,978,704 | A | | 11/1999 | Ideker et al. | |
| 5,978,705 | A | | 11/1999 | KenKnight et al. | |

(List continued on next page.)

FOREIGN PATENT DOCUMENTS

| WO | WO 97/25098 | 7/1997 |
|---|---|---|
| WO | WO 00/13748 | 3/2000 |
| WO | WO 00/66222 | 11/2000 |

OTHER PUBLICATIONS

US 5,584,866, 12/1996, Kroll et al. (withdrawn)
Brown et al.; "Estimating the Duration of Ventricular Fibrillation" *Annals of Emergency Medicine* 18:11 1181–1185 (1989).
Brown et al.; "Median Frequency—A New Parameter for Predicting Defibrillation Success Rate" *Annals of Emergency Medicine* 20:7 787–789 (1991).

(List continued on next page.)

*Primary Examiner*—Scott M. Getzow
(74) *Attorney, Agent, or Firm*—Myers Bigel Sibley & Sajovec

(57) ABSTRACT

A method of reducing the likelihood of pulseless electrical activity (PEA) after defibrillation in a subject comprises administering to a subject afflicted with fibrillation a first treatment waveform, the first treatment waveform insufficient to defibrillate the heart; and then administering to the subject a second treatment waveform that defibrillates the heart and restores organized electrical activity in the heart. The first treatment waveform reduces the likelihood of onset of PEA following the second treatment waveform, as compared to that likelihood which would be present in the absence of the first treatment waveform.

148 Claims, 14 Drawing Sheets

U.S. PATENT DOCUMENTS

| | | | |
|---|---|---|---|
| 5,987,354 A | 11/1999 | Cooper et al. | |
| 6,002,962 A | 12/1999 | Huang et al. | |
| 6,041,254 A | 3/2000 | Sullivan et al. | 607/5 |
| 6,041,255 A | 3/2000 | Kroll | 607/5 |
| 6,047,212 A | 4/2000 | Gliner et al. | 607/7 |
| 6,088,616 A | 7/2000 | Olson et al. | 607/5 |
| 6,125,298 A | 9/2000 | Olson et al. | |
| 6,167,306 A | 12/2000 | Kroll | 607/5 |
| 6,185,457 B1 | 2/2001 | Kroll | 607/5 |
| 6,298,267 B1 | 10/2001 | Rosborough et al. | |
| 6,314,319 B1 | 11/2001 | Kroll | 607/5 |

OTHER PUBLICATIONS

Brown, et al.; "Signal Analysis of the Human Electrocardiogram During Ventricular Fibrillation: Frequency and Amplitude Parameters as Predictors of Successful Countershock" *Annals of Emergency Medicine* 27:2 184–188 (1996).

McDaniel et al.; "The Cardiac Ventricular Defibrillation Threshold: Inherent Limitations in Its Application and Interpretation" *Medical Instrumentation* 21:3 170–176 (1987).

Strohmenger et al.; "Analysis of the ventricular fibrillation ECG signal amplitude and frequency parameters as predictors of countershock success in humans" *Chest* 111:3 584–589 (1997).

Povoas, H.P., et al., *Electrocardiographic waveform analysis for predicting the success of defibrillation*; Crit Care Med, vol. 28 (11 Suppl), Abstract, pp. N210–1 (Nov. 2000).

Callaway, C.W., et al., *Scaling structure of electrocardiographic waveform during prolonged ventricular fibrillation in swine*, Pacing & Clinical Electrophysiology, vol. 23, No. 2, Abstract, pp. 180–191 (Feb. 2000).

Brown, C.G., et al., *Physiologic measurement of the ventricular fibrillation ECG signal: estimating the duration of ventricular fibrillation*, Annals of Emergency Medicine, vol. 22, No. 1, Abstract, pp. 70–74 (Jan. 1993).

Rosborough, John P., et al., *Electrical Therapy for Pulseless Electrical Activity*, PACE, vol. 23, Part II, Abstract, p. 591 (Apr. 2000).

Eftestøl, Trygve, et al., *Predicting Outcome of Defibrillation by Spectral Characterization and Nonparametric Classification of Ventricular Fibrillation in Patients with Out–of–Hospital Cardiac Arrest*, Circulation, pp. 1523–1529 (Sep. 26, 2000).

Sabbah, Hanl N., et al., *Delivery of Non–Excitatory Contractility–Modulation Electric Signals Improve Left Ventricular Performance in Dogs with Heart Failure*, Circulation, vol. 100, Abstract, p. 1–122 (1999).

Prulchi, David, et al., *An Implantable Device to Enhance Cardiac Contractility through Non–Excitatory Signals*, Circulation, vol. 100, Abstract, p. 1–300 (1999).

Papone, Carlo, et al., *First Clinical Experience Demonstrating Improvement of Hemodynamic Parameters in Heart Failure Patients Through the Application of Non–Excitatory Electrical Signals*, JACC, vol. 35, Abstract, p. 229A (2000).

Shemer, Itzhak, et al., *Myocardial Contractility Modulation Using a Non–Excitatory Electrical Signal*, JACC, vol. 35, Abstract, p. 148A (2000).

International Search Report dated Jun. 5, 2002 for International Application No. PCT/US01/44089.

T. Tokano, D. Bach, J. Chang, J. Davis, J. J. Souza, A. Zivin, B. P. Knight, R. Goyal, K. C. Man, F. Morady, and S. A. Strickberger. Effect of ventricular shock strength on cardiac hemodynamics. *Cardiovasc Electrophysiol*, 9(8):791–7, Aug. 1998.

M. M. Amirhamzeh, C. X. Jia, W. M. Park, M. L. Dickstein, and H. M. Spotnitz. Systolic arterial pressure recovery after ventricular fibrillation in pigs. *Ann Thorac Surg*, 58(5):1374–9, Nov. 1994.

W. M. Park, M. M. Amirhamzeh, C. X. Jia, M. R. Bielefeld, S. E. Cabreriza, M. L. Dickstein, and H. M. Spotnitz. Systolic arterial pressure recovery after ventricular fibrillation/flutter in humans. *Pacing Clin Electrophysiol*, 17(6):1100–6, Jun. 1994.

Thijs LG, Vincent JL, Weil MH, Michaels WS, and Carlson R. A closed–chest model for the study of electromechanical dissociation of the heart in dogs. *Resuscitation*, 10(1):25–32, Mar. 1982.

Wood EH. Action potential control of cardiac contractility. *Ann Biomed Eng*, 28(8):860–70, Aug. 2000.

Wood EH, Heppner RL, and Weidmann S. Inotropic effects of electric currents. i. positive and negative effects of constant electric currents or current pulses applied during cardiac action potentials. ii. hypotheses: calcium movements, excitation–contraction coupling and inotropic effects. *Circ Res*, 24(3):409–45, Mar. 1969.

R. C. Park, W. C. Little, and R. A. O'Rourke. Effect of alteration of left ventricular activation sequence on the left ventricular end–systolic pressure–volume relation in closed–chest dogs. *Circ Res*, 57(5):706–17, Nov. 1985.

Mansourati J, Etienne Y, Gilard M, Valls–Bertault V, Boschat J, Benditt DG, Lurie KG, and Blanc JJ. Left ventricular–based pacing in patients with chronic heart failure: comparison of acute hemodynamic benefits according to underlying heart disease. *Eur J Heart Fail*, 2(2):195–9, Jun. 2000.

Blanc JJ., Etienne Y, Gilard M, Mansourati J, Munier S, Boschat J, Benditt DG, and Lurie KG. Evaluation of different ventricular pacing sites in patients with severe heart failure: results of an acute hemodynamic study. *Circulation*, 96(10):3273–7, Nov. 18, 1997.

W. C. Randall, J. P. Pace, J. S. Wechsler, and K. S. Kim. Cardiac responses to separate stimulation of sympathetic and parasympathetic components of the vagosympathetic trunk in the dog. *Cardiology*, 54(2):104–18, 1969.

M. H. Huang, F. M. Smith, and J. A. Armour. Modulation of in situ canine intrinsic cardiac neuronal activity by nicotinic, muscarinic, and beta–adrenergic agonists. *Am J Physiol*, 265(3 Pt 2): R659–69, Sep. 1993.

W. C. Randall, D. V. Priola, J. B. Pace, and J. S. Wechsler. Ventricular augmentor fibers in the cervical vagosympathetic trunk. *Proc Soc Exp Biol Med*, 124(4):1254–8, Apr. 1967.

J. R. Blinks. Field stimulation as a means of effecting the graded release of autonomic transmitters in isolated heart muscle. *J Pharmacol Exp Ther*, 151(2):221–35, Feb. 1966.

W. C. McDaniel and J. C. Schuder. The cardiac ventricular defibrillation threshold: inherent limitations in its application and interpretation. *Med Instrum*, 21(3):170–6, Jun. 1987.

D. G. Pansegrau and F. M. Abboud. Hemodynamic effects of ventricular defibrillation. *J Clin Invest*, 49(2):282–97, Feb. 1970.

R. E. Kerber, J. B. Martins, J. A. Gascho, M. L. Marcus, and J. Grayzel. Effect of direct–current countershocks on regional myocardial contractility and perfusion. experimental studies. *Circulation*, 63(2):323–32, Feb. 1981.

W. Flacke and R. A. Gillis. Impulse transmission via nicotinic and muscarinic pathways in the stellate ganglion of the dog. *J Pharmacol Exp Ther*, 163(2):266–76, Oct. 1968.

C. K. Butler, F. M. Smith, R. Cardinal, D. A. Murphy, D. A. Hopkins, and J. A. Armour. Cardiac responses to electrical stimulation of discrete loci in canine atrial and ventricular ganglionated plexi. *Am J Physiol*, 259(5 Pt 2): H1365–73, Nov. 1990.

A. J. Brady, B. C Abbott, and W. F. H. M Mommaerts. Ionotropic effects of trains of impulses applied during the contraction of cardiac muscle. *The Journal of General Physiology*, 44:415–432, 1960.

D. V. Exner, J. A. Reiffel, A. E. Epstein, R. Ledingham, M. J. Reiter, Q. Yao, H. J. Duff, D. Follmann, E. Schron, H. L. Greene, M. D. Carlson, M. A. Brodsky, T. Akiyama, C. Baessler, and J. L. Anderson. Beta–blocker use and survival in patients with ventricular fibrillation or symptomatic ventricular tachycardia: the antiarrhythmics versus implantable defibrillators (avid) trial. *J Am Coll Cardiol*, 34(2):325–33, Aug. 1999.

\* cited by examiner

METHOD FOR IMPROVING CARDIAC FUNCTION FOLLOWING DELIVERY OF A DEFIBRILLATION SHOCK

RELATED APPLICATIONS

This application is a continuation-in-part of commonly owned, U.S. patent application Ser. No. 09/772,225, filed Jan. 29, 2001, now U.S. Pat. No. 6,556,856 the disclosure of which is incorporated by reference herein in its entirety.

FIELD OF THE INVENTION

The present invention concerns methods for improving cardiac function and reducing the occurrence of pulseless electrical activity after the delivery of a defibrillation pulse to a subject.

BACKGROUND OF THE INVENTION

Sudden cardiac death (SCD) accounts for an estimated 200,000 to 400,000 deaths annually in the United States alone. The initial cardiac rhythm in the majority of SCD cases is ventricular fibrillation (VF). Only approximately 10% of all SCD victims will be discharged from the hospital despite prompt CPR, a good emergency medical system response time, and use of automatic external defibrillators.

Approximately 50% of SCD patients will be treated with a defibrillator, by which they are administered a defibrillation waveform. Of the "successful" defibrillations, approximately 50% will exhibit an electrical pulse as demonstrated by an electrocardiogram, but will not exhibit a physical pulse as demonstrated by restored, peripherally measured, blood pressure. This condition is known as "pulseless electrical activity" (PEA) or "electromechanical dissociation" (EMD). Only approximately 8% of individuals with post-shock PEA survive to be discharged from the hospital. Hence, there is a clear need for ways to reduce the frequency or likelihood of onset of PEA to thereby increase the efficacy of defibrillation.

PCT Application WO 00/66222 to Rosborough and Deno describes a method and apparatus for treatment of cardiac electromechanical dissociation in which a first treatment signal to terminate a techyarrhythmia is administered to the heart of a subject, blood flow is measured, and if the measured blood flow is below a predetermined amount then a second signal, such as a series of packets of electrical pulses, is administered. One problem with such an approach is the need to wait until after defibrillation to monitor the patient before deciding whether to administer the post-treatment packets of pulses to treat the electromechanical dissociation.

U.S. Pat. No. 5,314,448 to Kroll et al. describes a process for defibrillation pretreatment of a heart in which an electrical pretreatment of a fibrillating heart is applied. The pretreatment is said to begin organizing the action of the chaotically contracting myocardial cells so that the defibrillating waveform applied after the pretreatment can accomplish its task with less energy than would otherwise be required. This reference is concerned with reducing shock energy and capacitor size for implantable defibrillation systems. This reference is not concerned with external defibrillation systems, is not concerned with treating PEA, and is not concerned with increasing the efficacy of defibrillation.

U.S. Pat. No. 5,978,705 to KenKnight et al. descries a method for treating cardiac arrhythmia in which an auxiliary pulse is delivered in conjunction with a primary pulse, with the auxiliary pulse being delivered to a weak field area relative to the primary pulse. The object of the auxiliary pulse is to alter the intrinsic patterns of recovery of excitability and thereby momentarily yield localized cessation of propagation by inactivating sodium ion conductance channels via elevation of the transmembrane potential (see, e.g., column 8, lines 59–66). This reference is not concerned with the treatment of PEA.

Accordingly, there remains a need for new ways to treat and reduce pulseless electrical activity, particularly PEA following the administration of a defibrillation waveform.

SUMMARY OF THE INVENTION

A first aspect of the present invention is a method of reducing the likelihood of onset of pulseless electrical activity after defibrillation in a subject afflicted with a fibrillating heart. The method comprises administering to a subject afflicted with fibrillation a first treatment waveform, the first treatment waveform insufficient to defibrillate the heart; and then administering to the subject a second treatment waveform that defibrillates the heart and restores organized electrical activity in the heart. The first treatment waveform reduces the likelihood of onset of pulseless electrical activity following the second treatment waveform, as compared to that likelihood which would be present in the absence of the first treatment waveform.

A second aspect of the present invention is a system for the defibrillation of the heart of a patient in need of such treatment. The system comprises a power supply and a controller operatively associated with the power supply, the controller configured for delivering a defibrillation sequence comprising a first treatment waveform, the first treatment waveform insufficient to defibrillate the heart, and then a second treatment waveform that defibrillates the heart and restores organized electrical activity in the heart. The first treatment waveform reducing the likelihood of onset of pulseless electrical activity following the second treatment waveform as compared to that likelihood which would be present in the absence of the first treatment waveform.

A third aspect of the present invention is a method for the external defibrillation of the heart of a patient afflicted with ventricular fibrillation. The method comprises externally administering to the patient a first treatment waveform, the first treatment waveform insufficient to defibrillate the heart, and then externally administering to the subject a second treatment waveform that defibrillates the heart and restores organized electrical activity in the heart.

A fourth aspect of the present invention is an external defibrillation system for the external defibrillation of the heart of a patient afflicted with ventricular fibrillation. The system comprises a power supply and a controller operatively associated with the power supply. The controller is configured for delivering a defibrillation sequence comprising a first treatment waveform, the first treatment waveform insufficient to defibrillate the heart, and then a second treatment waveform that defibrillates the heart and restores organized electrical activity in the heart.

A fifth aspect of the present invention is a method of reducing the likelihood of onset of pulseless electrical activity after defibrillation with an implantable defibrillator in a subject afflicted with a fibrillating heart. The method comprises the steps of administering to a subject afflicted with fibrillation a first treatment waveform, the first treatment waveform insufficient to defibrillate the heart, and then administering to the subject a second treatment waveform that defibrillates the heart and restores organized electrical activity in the heart. The first treatment waveform reduces the likelihood of onset of pulseless electrical activity following the second treatment waveform as compared to that likelihood which would be present in the absence of the first treatment waveform.

A sixth aspect of the present invention is an implantable defibrillator for defibrillating the heart of a subject in need thereof. The defibrillator comprises a power supply and a controller operatively associated with the power supply. The controller is configured for delivering a defibrillation sequence comprising a first treatment waveform, the first treatment waveform insufficient to defibrillate the heart; and then a second treatment waveform that defibrillates the heart and restores organized electrical activity in the heart. The first treatment waveform reduces the likelihood of onset of pulseless electrical activity following the second treatment waveform as compared to that likelihood which would be present in the absence of the first treatment waveform.

A further aspect of the present invention is a defibrillation system for the defibrillation of the heart of a patient afflicted with ventricular fibrillation. The system comprises a detector for detecting electrical activity from the heart of said patient during ventricular fibrillation; a power supply; a signal analyzer operatively associated with said detector and configured for determining the likelihood of pulseless electrical activity in said patient after delivery of a defibrillation treatment waveform to said patient; and a controller operatively associated with said power supply and said signal analyzer, said controller configured for delivering a defibrillation sequence, said defibrillation sequence optionally comprising a first treatment waveform, said first treatment waveform insufficient to defibrillate said heart, and then delivering a second treatment waveform that defibrillates said heart and restores organized electrical activity in said heart. The first treatment waveform is delivered when a high likelihood of pulseless electrical activity after defibrillation is determined, and said first treatment waveform is not delivered when a low likelihood of pulseless electrical activity after defibrillation is determined.

The foregoing and other objects and aspects of the present invention are explained in greater detail in the drawings herein and the specification below.

DETAILED DESCRIPTION OF THE PREFERRED EMBODIMENTS

Pulseless electrical activity (PEA) herein refers to all types of pulseless electrical activity, including post-defibrillation shock PEA, "pseudo" PEA (i.e., wherein an increase in pressure in the left ventricle occurs, but does not reach the arteries), true PEA (i.e., a patient found in a state of PEA), and normotensive PEA. The term PEA herein is intended to include cardiac electromechanical dissociation (EMD). While all types of PEA may be treated by the method of the present invention, the treatment of post-shock, post-cardioversion or post-defibrillation PEA is a particular object herein.

Subjects that may be treated by the method of the present invention include both human subjects and animal subjects (particularly mammalian subjects such as dogs, cats, etc.) for both medical and veterinary purposes. Human subjects are particularly suitable for treatment with the methods and apparatus described herein.

1. Defibrillation Sequences

As noted above, the present invention provides a defibrillation sequence comprised of a first treatment waveform and a second treatment waveform. In general, the first treatment waveform is insufficient to defibrillate the subject and may be insufficient to reduce the defibrillation threshold of the subject, but serves to reduce the occurrence or likelihood of occurrence of PEA in the subject. The second treatment waveform is the defibrillation waveform, which serves to restore organized electrical activity in the heart of the subject to which the defibrillation sequence is administered.

Without wishing to be limited to any particular theory of the invention, it is presently believed that the instant invention operates by stimulating (in whole or in part) the sympathetic innervation to the heart, achieving an effect similar to the administration of epinephrine. In the alternative, the first treatment pulse may increase intracellular calcium levels.

Figure 1A:
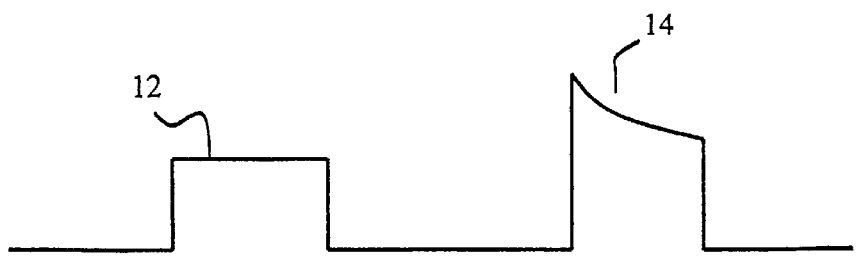
FIG. 1A illustrates an embodiment of a defibrillation sequence of the present invention.
Figure 1B:
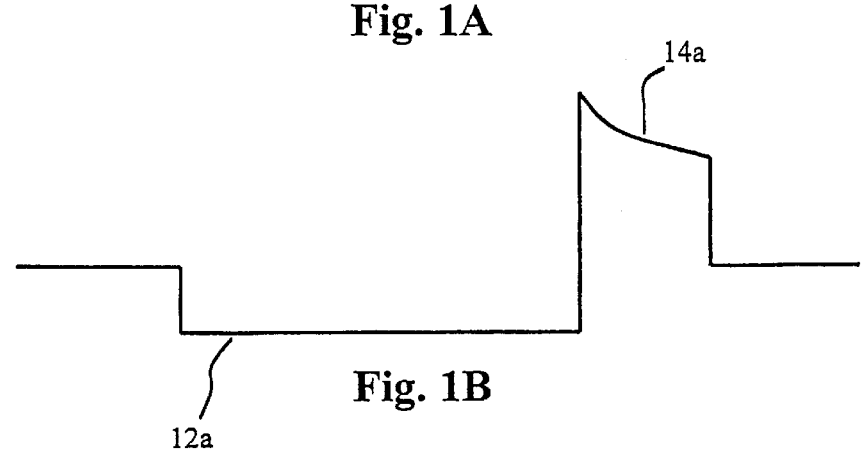
FIG. 1B illustrates a second embodiment of a defibrillation sequence of the present invention.
Figure 1C:
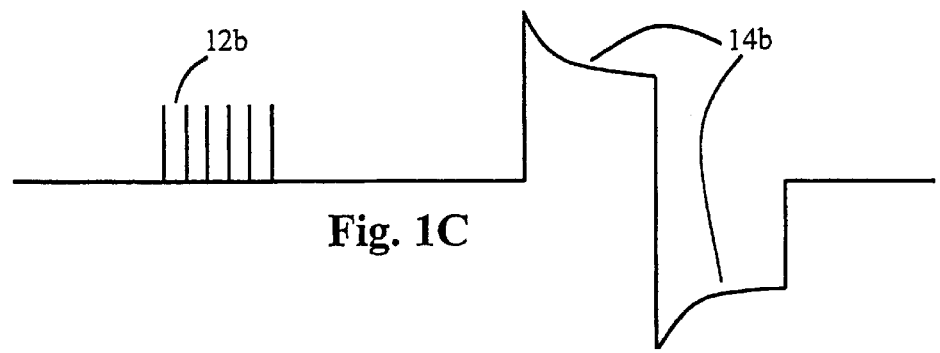
FIG. 1C illustrates a third embodiment of a defibrillation sequence of the present invention.
Figure 1D:
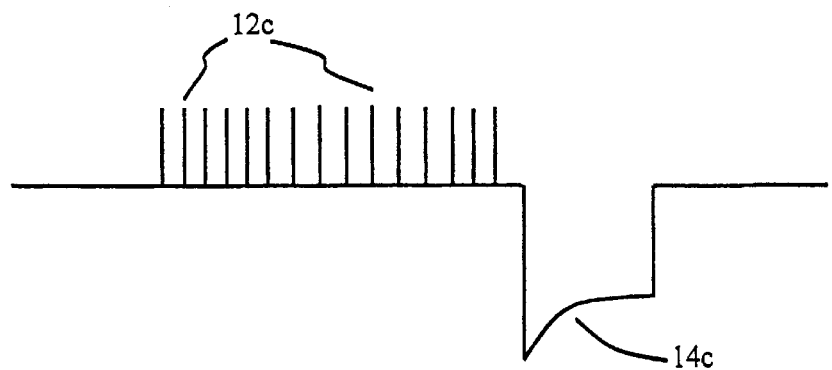
FIG. 1D illustrates a fourth embodiment of a defibrillation sequence of the present invention.

As illustrated in FIGS. 1A–1D, the present invention may be practiced in a variety of different ways. For example, FIG. 1A illustrates an embodiment of a defibrillation sequence of the present invention, in which the first treatment waveform 12 is a single pulse separate in time from the second treatment waveform 14. A second embodiment is illustrated in FIG. 1B, in which the first treatment waveform 12*a* is a single pulse that is not separate in time from the second treatment waveform 14*a*, and is also of opposite polarity from the second treatment waveform. A third embodiment is illustrated in FIG. 1C, in which the first treatment waveform 12*b* is a series of pulses that are separate in time from the second treatment waveform 14*b*, and in which the second treatment waveform is a biphasic treatment waveform. A fourth embodiment is illustrated in FIG. 1D, in which the first treatment waveform 12*c* is a series of pulses, are not substantially separated in time from the second treatment waveform 14*c*, and are of opposite polarity from the second treatment waveform. Numerous additional variations and alternate embodiments will be readily apparent to those skilled in the art.

In general, the properties of the first treatment waveform, such as polarity, shape, periodicity, etc., are not critical, so long as the first treatment waveform is below the defibrillation threshold. For example, The first waveform may be of any suitable duration, for example from about 0.1, 1 or 10 milliseconds to 1, 5 or 10 seconds or more. When the first treatment waveform is administered by external electrodes it may have an energy of from about 1, 2 5 or 10 Joules to 50, 100, or 200 Joules. When the first treatment waveform is administered by internal electrodes it may have an energy of from about 0.1, 1 or 2 to 20, 40 or 50 Joules.

The properties of the second treatment waveform are also not critical, so long as the second treatment waveform is above the defibrillation threshold. For example, the second treatment waveform may be monopolar or bipolar (as in FIG. 1B), a square wave or a truncated exponential waveform, may be of the same polarity of the first treatment waveform (as in FIG. 1A) or opposite polarity (as in FIG. 1B and FIG. 1D) to the first treatment waveform, etc. The second treatment waveform may comprise a single waveform, as described, or (particularly for internal defibrillators) may itself comprise a plurality of waveforms delivered across multiple current pathways.

As will be appreciated from FIGS. 1A–D, the first treatment waveform and the second treatment waveform are sequential or substantially sequential. The second treatment waveform may immediately follow the first treatment waveform (as illustrated in FIG. 1B and FIG. 1D). The second treatment waveform may follow the first treatment waveform by a gap or separation in time between the delivery of the two waveforms (as illustrated in FIG. 1A and FIG. 1C), the separation in time being from 1 or 10 millisecond to 5 or 10 seconds. The first treatment waveform and the second treatment waveform may be at least partially interleaved, which can be accomplished both by delivering the waveforms through different electrodes, by delivering different amplitude waveforms through the same electrodes, or combinations thereof.

As noted above, the first treatment waveform and the second treatment waveform may be delivered through the same, or different, electrodes. The waveforms (e.g., the first treatment waveform) may be delivered with any suitable defibrillation apparatus, certain preferred embodiments of which are discussed in greater detail below. In general, the first treatment waveform may be delivered by at least one cutaneous electrode (e.g., a pair of cutaneous electrodes), may be delivered by at least one subcutaneous electrode (e.g., a pair of subcutaneous electrodes), may be delivered by at least one transveneous electrode (e.g., a pair of transveneous electrodes), by combinations of such electrodes, etc.

The second treatment waveform may be of any suitable type sufficient to defibrillate the patient. The particular form or type of the second treatment waveform is not critical. In general, the second treatment waveform may be a single electrical pulse or multiple electrical pulses; the second treatment waveform may be delivered along a single current pathway (which may be the same as or different from the current pathway of the first treatment waveform), or may be delivered along multiple current pathways. The second treatment waveform may be comprised of monophasic or biphasic electrical pulses of any suitable shape, such as a truncated exponential waveform.

2. Implantable Cardioverter/Defibrillators

Implantable cardioverter/defibrillators (ICDs) are known, and such known cardioverter/defibrillators may be modified and/or adapted for use in carrying out the present invention as described herein. Examples of suitable internal defibrillators include, but are not limited to, those described in U.S. Pat. Nos. 5,978,705 to KenKnight et al. and 5,978,704 to Ideker et al. Applicants specifically intend that the disclosures of all United States patent references cited herein be incorporated by reference herein in their entirety.

Figure 2:
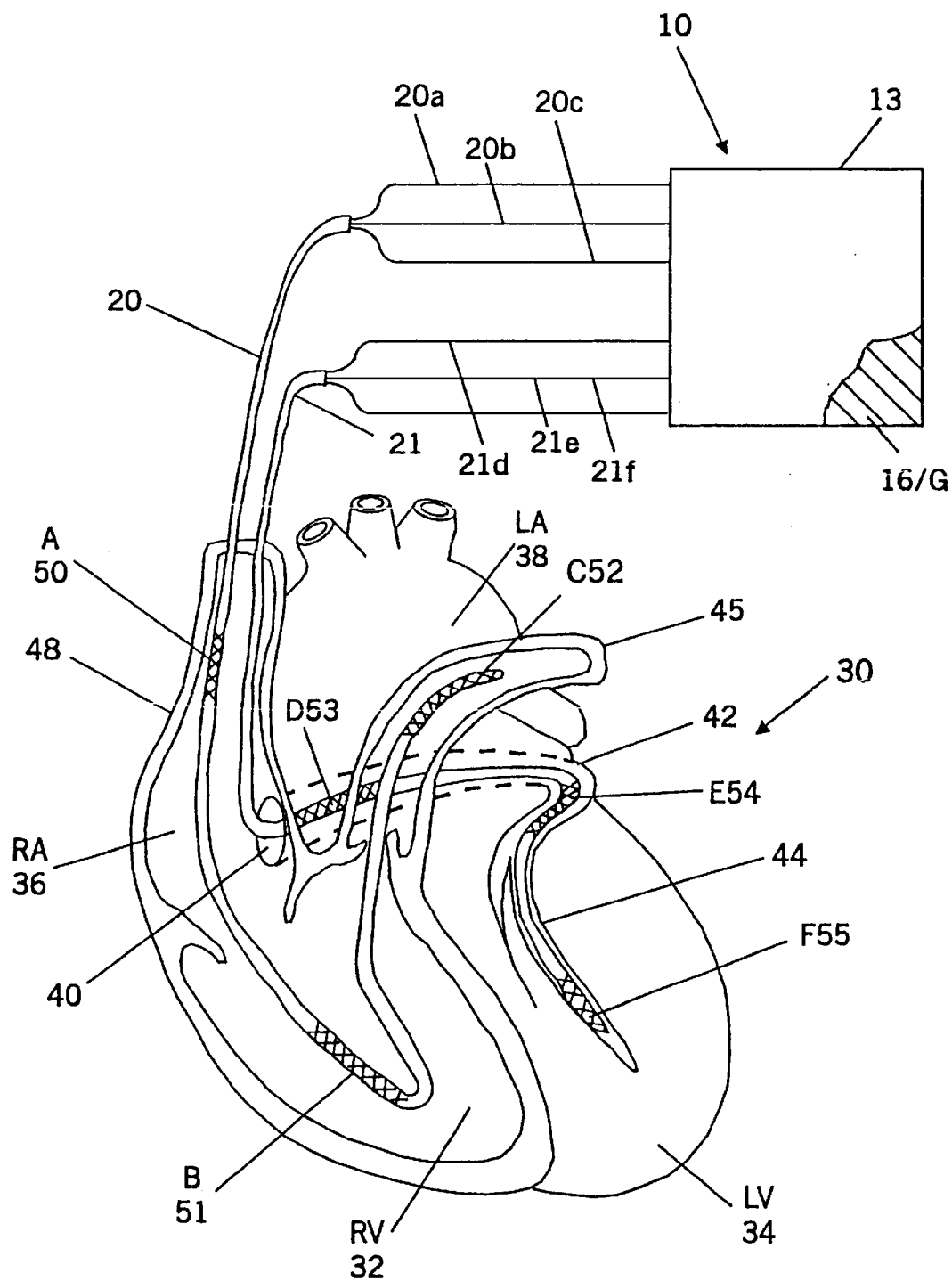
FIG. 2 illustrates an implantable cardioverter/defibrillator of the present invention.

The schematically illustrated portions of the heart 30 illustrated in FIG. 2 includes the right ventricle "RV" 32, the left ventricle "LV" 34, the right atrium "RA" 36, the left atrium "LA" 38, the superior vena cava 48, the coronary sinus "CS" 42, the great cardiac vein 44, the left pulmonary artery 45, and the coronary sinus ostium or "os" 40.

Various embodiments of the present invention can be illustrated with reference to FIG. 2. The implantable cardioverter/defibrillator 10 of FIG. 2 includes an implantable housing 13 that contains a hermetically sealed electronic circuit 15 (see FIG. 2). The housing optionally, but preferably, includes an electrode comprising an active external portion 16 of the housing, with the housing 13 preferably implanted in the left thoracic region of the patient (e.g., subcutaneously, in the left pectoral region) in accordance with known techniques as described in G. Bardy, U.S. Pat. No. 5,292,338. The system includes a first catheter 20 and a second catheter 21, both of which are insertable into the heart (typically through the superior or inferior vena cava) without the need for surgical incision into the heart. The term "catheter" as used herein includes "stylet" and is also used interchangeably with the term "lead". Each of the catheters 20, 21 contains electrode lead wires 20*a,* 20*b,* 20*c,* 21*d,* 21*e,* and 21*f,* respectively, with the small case letter designation corresponding to the large-case letter designation for the defibrillation electrode to which each lead wire is electrically connected.

As illustrated in FIG. 2, the catheter 20 includes an electrode A; 50 that resides in the right atrium (the term "right atrium" herein including the superior vena cava and innominate vein), an electrode B; 51 positioned in the right ventricle (preferably in the right ventricular apex), and an electrode C; 52 positioned within the left pulmonary artery (the term "left pulmonary artery" herein includes the main pulmonary artery and the right ventricular outflow tract).

The second catheter 21 includes, from proximal to distal, a first electrode D; 53 positioned in the proximal coronary sinus, adjacent the coronary sinus ostium or "os" 40; a second electrode E; 55 positioned in the distal coronary sinus (preferably as far distal in the coronary sinus as possible) (the term "distal coronary sinus" herein includes the great cardiac vein); and a third electrode F; 56 at or adjacent the tip of the catheter in a coronary vein on the surface (preferably the posterolateral surface) of the left ventricle (e.g., in the lateral-apical left ventricular free wall). Electrode A, 52 may optionally be positioned on lead 21 and retain the same operable positions described above as when positioned on lead 20. The active external portion of the housing 16 serves as an optional seventh electrode G, which may be used for either atrial or ventricular defibrillation. It will be appreciated that, while the illustrated device is a combined atrial and ventricular ICD, the present invention can be similarly implemented with a ICD adapted for treatment of the ventricles alone.

The electrodes described in FIG. 2 and the specification above may, for convenience, be designated by the most adjacent structure. These structures are: the right atrium (RA), right ventricle (RV), pulmonary artery (PA), coronary sinus ostium (OS), distal coronary sinus (CS), and left ventricle (LV). Thus, when applied to electrodes the electrodes of FIG. 2: RA means electrode A, 50; RV means electrode B, 51; PA means electrode C, 52; OS means electrode D, 53; CS means electrode E, 54; and LV means electrode F, 55.

Figure 3:
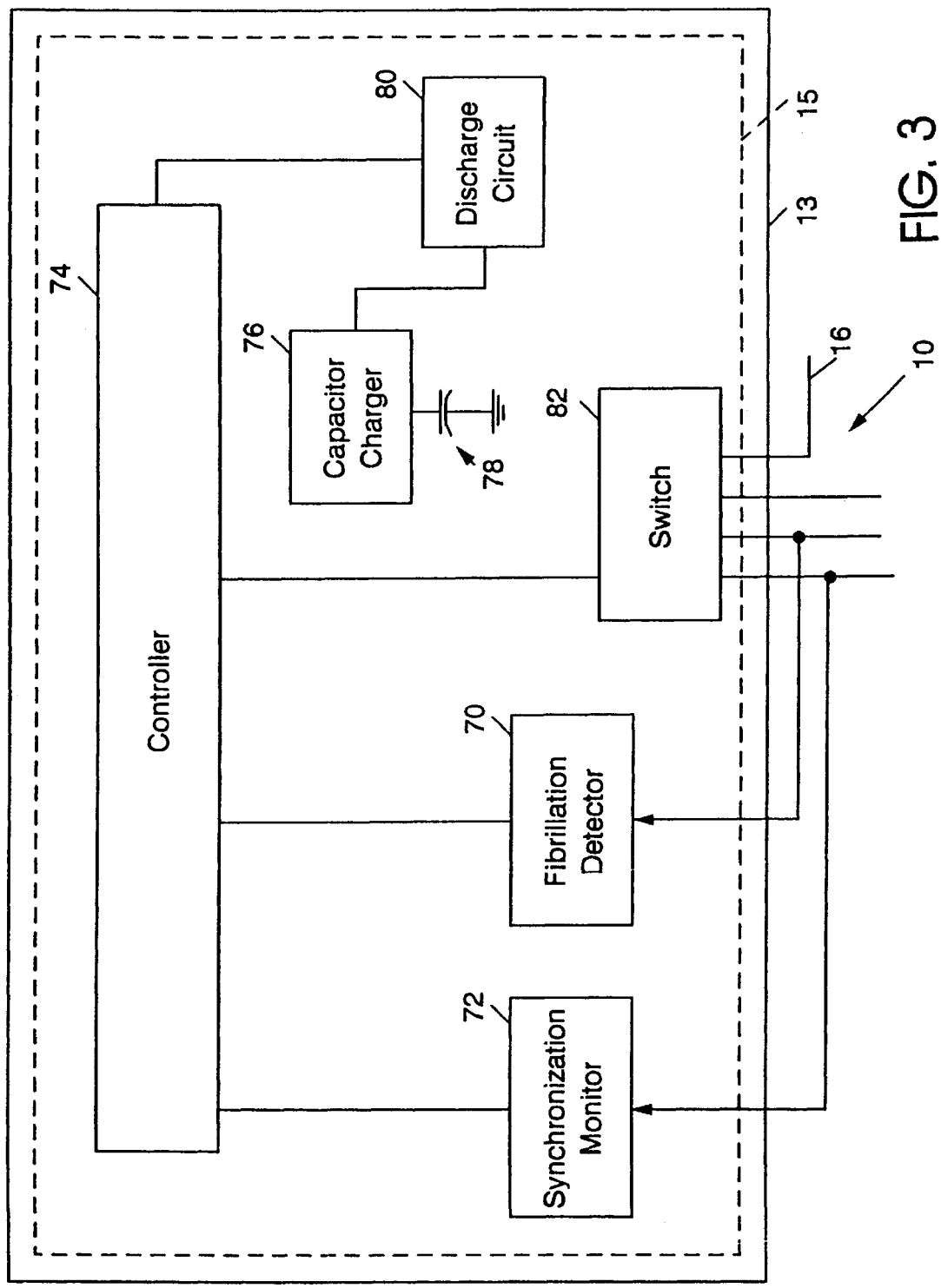
FIG. 3 schematically illustrates control circuitry in an implantable cardioverter/defibrillator according to FIG. 2.

FIG. 3 illustrates one example of an implantable housing 13 containing an electronic circuit 15, which includes one or more amplifiers (not shown) for amplifying sensed cardiac signals. The amplified signals are analyzed by a atrial and ventricular fibrillation detector 70 which determines if ventricular fibrillation (or other arrhythmia, depending on the specific treatment for which the device is configured) is present. The detector 70 may be one of several known to those skilled in the art. As illustrated, a sensing signal may be provided by the electrode A 50, it will be appreciated by those of skill in the art that the sensing electrode may also be a plurality of sensing electrodes with a plurality of signals, such as bipolar configurations, and may also be electrodes that are positioned in alternate cardiac areas as is known in the art, such as for example, the CS. In this situation, the input line to the detector may be a plurality of lines which if providing only sensing will provide an input to the detector.

Ventricular sensing for timing the shocks for atrial defibrillation may be performed from the RV and/or LV electrodes.

The defibrillation electrodes may alternately be configured to sense cardiac cycles, or may have smaller sensing electrodes placed adjacent thereto and thereby provide input to the electronics package as well as provide a predetermined stimulation shock output to predetermined cardiac areas as directed by the controller.

The electronic circuit 15 also includes a cardiac cycle monitor ("synchronization monitor 72") for providing synchronization information to the controller 74. As discussed below, the synchronization is typically provided by sensing cardiac activity in the RV, but may also include other sensing electrodes which can be combined with the defibrillation electrodes or employed separately to provide additional assurance that defibrillation shock pulses are not delivered during sensitive portions of the cardiac cycle so as to reduce the possibility of inducing ventricular fibrillation.

Upon a signal from the detector 70, the controller 74, in turn, signals a capacitor charging circuit 76 which then charges the storage capacitor 78 to a predetermined voltage, typically from a battery source (not shown). The storage capacitor is typically 20 to 400 microfarads in size, and may be a single capacitor or a capacitor network (further, as discussed below, separate pulses can be driven by the same or different capacitors). The discharge of the capacitor is controlled by the controller 74 and/or a discharge circuit 80. The controller, based on information from the synchronization monitor 72, typically allows or directs the preselected shock pulse to be relayed to either a discharge circuit for further processing (i.e., to further shape the waveform signal, time the pulse, etc.) or directly to a switch. The controller may also control the proper selection of the predetermined defibrillation electrode pair(s), where multiple defibrillation electrodes are used, to direct the switch to electrically activate a desired electrode pair to align the predetermined electric shock pulse pathway through which the shock pulse is provided. As an alternative to a detector, the defibrillation pulses may be triggered by an external signal administered by a physician, with the physician monitoring the patient for the appropriate time of administration.

Numerous configurations of capacitor and control circuitry may be employed. The power supply may include a single capacitor, and the controller may be configured so that both the auxiliary pulse and the defibrillation pulse are generated by the discharge of the single capacitor. The power supply may include a first and second capacitor, with the controller configured so that the auxiliary pulse is generated by the discharge of the first capacitor and the defibrillation pulse is generated by the discharge of the second capacitor. In still another embodiment, the power supply includes a first and second capacitor, and the controller may be configured so that the auxiliary pulse is generated by the discharge (simultaneous or sequential) of both the first and second capacitors, and the defibrillation pulse likewise generated by the discharge of the first and second capacitors.

As illustrated by Table 1 below, taken from U.S. Pat. No. 5,978,704, numerous different combinations of electrodes from those shown in FIG. 2 may be employed to carry out ventricular defibrillation. The same electrodes may be employed for delivery of the first treatment waveform. In Table 1, polarity of electrode is illustrated by the direction of the arrows, but polarity is not critical and can be reversed.

TABLE 1

|   | Electrode Configuration |
|---|---|
| 1 | RA -> RV |
| 2 | PA -> LV |
| 3 | RA -> LV |
| 4 | PA -> RV |
| 5 | RV -> LV |

As will be seen from Table 1 of U.S. Pat. No. 5,978,704, a combination atrial and ventricular ICD may employ some or all of the electrodes illustrated in FIG. 2, and numerous combinations thereof.

Those skilled in the art will appreciate that still additional electrode combinations are possible by employing the "active can" electrode G, 16. In addition, multiple electrodes can be electrically coupled or "tied" together to form a single pole. For example, a shock can be delivered from either the RV or LV as one pole to the PA and OS tied together as the other pole.

Any suitable waveform may be used to carry out the present invention, including both monophasic and biphasic waveforms. Amplitude, polarity, and duration of waveforms are not critical and will be apparent to those skilled in the art, particularly in light of the further discussion below.

One preferred embodiment of the foregoing apparatus is an implantable system for the defibrillation of the ventricles of the heart of a patient in need of such treatment. The system comprises a plurality of primary electrodes, at least one auxiliary electrode, a power supply, and a controller. The plurality of primary electrodes are configured for delivering a defibrillation pulse along a predetermined current pathway in a first portion of the heart, the current pathway defining a weak field area in a second portion of the heart. At least one auxiliary electrode is configured for delivering an auxiliary pulse to the weak field area, with the at least one auxiliary electrode configured for positioning through the coronary sinus and in a vein on the surface of the left ventricle of the heart. The controller is operatively associated with the primary electrodes, the at least one auxiliary electrode, and the power supply, the controller configured for delivering a therapeutic sequence as described above.

Systems as described above may be implanted in a patient by conventional surgical techniques, or techniques readily apparent to skilled surgeons in light of the disclosure provided herein, to provide an implanted defibrillation or cardioversion system.

Additional features can also be added to the invention without affecting the function of the invention and result thereof. Such additional features include, but are not limited to, safety features such as noise suppression or multiple wave monitoring devices (R and T), verification checking to reduce false positive, precardioversion warning, programmed delayed intervention, bipolar configured sensing electrodes, intermittently activated defibrillation detector to reduce energy drain, a switching unit to minimize lines from the pulse generator, etc.

3. External Defibrillators

External defibrillators are also known, and such known external defibrillators may also be modified and/or adapted for use in carrying out the present invention as described herein. Examples of suitable external or manual defibrillators that are capable of delivering a ventricular defibrillation waveform include, but are not limited to, those described in U.S. Pat. Nos. 5,968,080; 5,902,323; 5,593,428; 6,047,212; 6,088,616; 6,041,255; 5,782,878; 5,700,281; 6,041,254; 5,824,017; 5,643,324; 5,645,571; and 5,593,428 (the disclosures of which are incorporated by reference herein in their entirety)

The external defibrillator may be of the type adapted for use by medical professionals. The external defibrillator may be an automatic external defibrillator (or "AED") which is adapted to be used by persons without extensive medical training, such as (for example) those described in U.S. Pat. Nos. 6,125,298 and 5,645,571 (the disclosures of which are incorporated herein by reference in their entirety).

Figure 4:
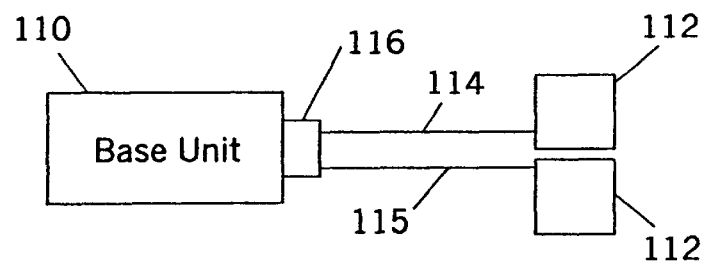
FIG. 4 illustrates an external defibrillator of the present invention.

An example external defibrillator 110 is illustrated in FIG. 4. The defibrillator comprises a base unit 111, to which electrodes 112, 113 are connected via leads 114, 115 connected through connection block 116. The base unit 111, illustrated in greater detail in FIG. 5, includes a charge and discharge circuitry 120 (typically comprising a battery and at least one discharge capacitor operatively associated with the battery through a charging circuit), and a controller 121 operatively associated with the charge and discharge circuit for monitoring the patient as appropriate and administering the defibrillation sequence to the patient.

Preferably the base unit includes a user interface 124 operatively associated with the controller for providing outputs to, and obtaining inputs from, the operator of the defibrillator. For example, the user interface may include a display, e.g., LEDs, LCD, or some combination thereof, for displaying the patient's ECG waveform and for displaying various system and patient parameters, features, instructions, functions, warnings, alerts, commands, etc. for information to or selection by the operator. In addition, the user interface may include various audio output devices, e.g., a speaker, audio or tactile signal generator, etc. for notifying the operator of various system and patient parameters, features, instructions, functions, warnings, alerts, commands, etc. Further the user interface may include various user input mechanisms, e.g., control and command buttons, touch screens, voice recognition software, keyboard, mouse or pen-based entry devices, etc., for enabling the operator to input various system and patient parameters, instructions, commands, etc.

In one embodiment of the present invention, the user interface generates a warning signal concurrently or simultaneously with the delivery of the first treatment waveform. Because the first treatment waveform may be of a longer duration than a conventional defibrillation pulse, the warning signal serves to decrease the chance that the operator, assistants or bystanders will come into contact with the subject during delivery of the therapeutic sequence. The user interface may generate a warning of any suitable type, such as an audio, visual, or tactile signal warning (e.g., warning buzzer or tone, flashing light, vibration, text prompt, spoken warning, etc.) A combination of multiple different warning signals may be generated, such as both a flashing light and a warning buzzer or tone. Preferably, the controller is configured warning signal will begin just prior to the delivery of the therapeutic sequence (e.g., at least one half of a second or one second prior to the delivery of the therapeutic sequence). The delivery of the therapeutic sequence, which directly or indirectly triggers the warning signal, may itself be triggered by any suitable means, such as activation of one or more control switches or sequences by the operator, contacting of the electrodes to the subject, and combinations thereof.

When the defibrillator is configured as an AED, then the base unit will typically comprise a case or housing containing the circuitry components noted above in FIG. 5 as well as a plurality of defibrillation electrodes affixed thereto, a plurality of defibrillation electrodes removably connected or removably stored therein, a combination of at least one electrode affixed thereto and at least one electrode removably stored therein, etc., so that the device may be rapidly and conveniently placed into use by the operator.

In one preferred embodiment of the invention, the discharge circuitry includes at least two discharge capacitors connected in parallel for generating the therapeutic sequence that is delivered to the subject through the defibrillation electrodes.

In another embodiment of the invention, the discharge circuitry includes a single discharge capacitor, with the discharge capacitor being at least 75, 100, 200, 300, 400 or 500 microfarads in capacity.

Figure 5:
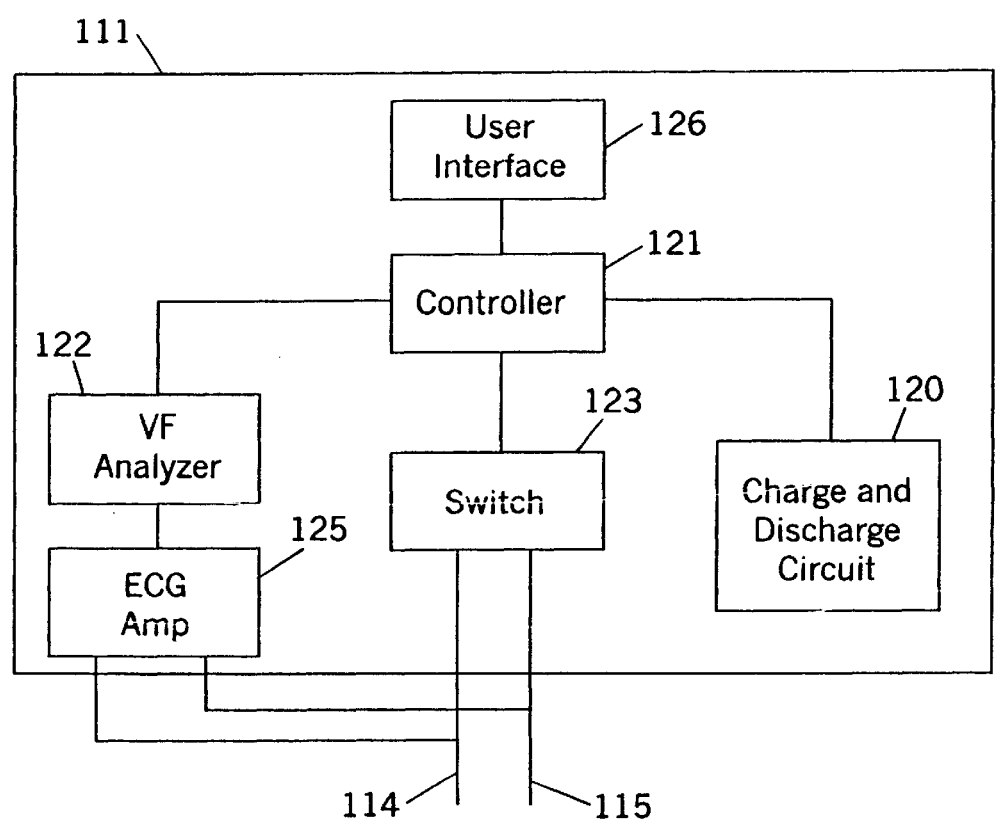
FIG. 5 illustrates control circuitry in an external defibrillator according to FIG. 4.

In the embodiment of the invention illustrated in FIG. 5, the external defibrillator further includes a signal analyzer 122 operatively associated with the controller 121 through which the likelihood of PEA after administration of a defibrillation shock is determined prior to administration of the shock. If a low likelihood of PEA is determined, then a defibrillation sequence may be selected that is comprised simply of a defibrillation waveform (i.e., corresponding to the "second" waveform herein); if a high likelihood of PEA is determined, then a defibrillation sequence may be selected that is comprised of a first treatment waveform and a second treatment waveform as described herein. If the external defibrillator is an AED, the likelihood of PEA will most often be determined automatically by the defibrillator itself by any suitable technique, such as by analyzing the spectrum or power spectrum of the waveform. See, e.g., Trygve Efestol, *Circulation* 102, 1523–1529 (2000). However, if the external defibrillator is a manual defibrillator or an AED placed in a manual mode, the likelihood of PEA may be determined manually by a fully trained operator based on his or her analysis of the patient's ECG waveform display and the appearance of the paitent. Further, in such a defibrillator, the operator not only may determine the likelihood of PEA, but the operator may also manually enable or disable the defibrillator to deliver the first treatment waveform as described herein.

The likelihood of a defibrillation shock resulting in PEA depends, at least in part, on the viability of the patient's heart, i.e., the ability of the heart to function mechanically, or pump blood, provided that an organized electrical rhythm can be restored. The heart becomes less viable as time passes in the absence of flow of oxygenated blood to the heart and the heart becomes metabolically deranged. This derangement may include decreased energy stores, increased intracellular calcium, decreased pH, increased extracellular potassium, and/or other anomalies. Accordingly, the viability of the heart, and thus the likelihood of PEA, depends on a variety of factors, such as duration of ventricular fibrillation, receipt of effective cardiopulmonary resuscitation (CPR), etc. Additionally, persons who have underlying cardiac disease, such as coronary artery disease, a previous myocardial infarction, or heart failure, may make a patient more likely to develop PEA than patients without these problems.

Consequently, the likelihood of PEA may be determined by assessing the viability of the heart. More specifically, in one embodiment of the present invention a numerical index or "viability index" that quantifies the condition of the heart is calculated and then used to determine whether the first treatment waveform described above is delivered to the patient. In another embodiment, multiple viability indices may be calculated, using different signals or different analysis techniques applied to the same signal or both, and used in combination to determine whether the first treatment described above is delivered to the patient. The viability index (or indices) may be determined in numerous ways, including but not limited to, analysis of the patient waveform during ventricular fibrillation, as a function of the duration the patient has been in ventricular fibrillation, as a function of physiological measurements indicative of blood flow, as a function of cardiac motion, or in accordance with user inputs.

Analysis of the Patient Waveform during Ventricular Fibrillation: There are a number of published techniques for analyzing the properties of the ventricular fibrillation waveform and estimating from that the viability of the heart. These publications describe analyses in which time and/or frequency domain techniques are used to extract information from the ECG signal, and they propose to use this information to estimate duration of ventricular fibrillation, to predict the likelihood of success of a subsequent defibrillation shock, or to advise caregivers whether the best resuscitative action would be to deliver CPR or to administer a defibrillation shock. In these publications, the information extracted from the ECG signal takes the form of various parameters such as the power spectrum of the ECG, the frequency and amplitude of the ECG, the median or centroid frequency of the ECG, and the scaling structure of the ECG. These quantities, as well as others, may be used alone or in combination as viability indices. Numerous techniques for analyzing patient waveforms that can be used to generate the viability indices mentioned above are known to those skilled in the art. See, e.g., C. Callaway et al., *Scaling structure of electrocardiographic waveform during prolonged ventricular fibrillation in swine,* Pacing & Clinical Electrophysiology 23, 180–91 (2000); P. Povoas and J. Bisera, *Electrocardiographic waveform analysis for predicting the success of defibrillation,* Crit. Care Med. 28 (11 Suppl), N210-1 (November 2000); H. Strohmenger et al., *Analysis of the ventricular fibrillation ECG signal amplitude and frequency,* Chest 111, 584–9 (1997); C. Brown and R. Dzwoncczyk, *Signal analysis of the human electrocardiogram during ventricular fibrillation: frequency and amplitude parameters as predictors of successful countershock,* Ann. Emerg. Med. 27, 184–8 (1996); C. Brown et al., *Median frequency—a new parameter for predicting defibrillation success rate,* Ann. Emerg. Med. 20, 787–9 (1991); C. Brown et al., *Estimating the duration of ventricular fibrillation,* Ann. Emerg. Med. 18, 1181–5 (1989).

Duration of Ventricular Fibrillation: The heart of a patient who has been in ventricular fibrillation for several minutes may be less viable. Thus, patients who have been in ventricular fibrillation for several minutes may benefit from electrotherapy for PEA. On the other hand, patients with very short duration ventricular fibrillation may not benefit from PEA electrotherapy. Accordingly, in one embodiment of the present invention, the duration of ventricular fibrillation is used to determine the viability index. Numerous techniques for measuring or estimating the duration of VF that can be used to generate a viability index are known to those skilled in the art. In one example, the properties of the ECG during ventricular fibrillation are used to estimate the duration of VF. See, e.g., C. Brown et al., *Physiologic measurement of the ventricular fibrillation ECG signal: estimating the duration of ventricular fibrillation,* Annals of Emergency Medicine 22, 70–74 (1993).

The viability of a heart in ventricular fibrillation for a relatively long period may also depend on other factors, e.g., a patient who has been in ventricular fibrillation for several minutes but who has received effective CPR for the last few minutes may have a more viable heart, and consequently a lower likelihood of developing PEA than a patient whose heart has not received any oxygenated blood during the period of fibrillation. Thus, it may be desirable to use other indices in combination with duration of fibrillation in deciding whether or not to deliver the first therapy.

Physiological Measurements: Physiologic measurements other than VF waveform characteristics (including duration) may be used alone or in combination with said characteristics to determine the viability index and estimate the likelihood that the heart will go into PEA following delivery of a defibrillation shock. Any measurements that are known to change systematically as the metabolic state of the body deteriorates in the absence of circulation may be applicable. Consequently, such measurements may be electrical, physical and/or chemical in nature. For example, electrical measurements may include parameters measured from the ECG or EEG (electroencephalogram) or transchest electrical impedance signals. Physical measurements may include patient temperature, invasive arterial or venous blood pressure, measures quantifying the motion of the heart during VF, measures of heart chamber volume, etc. Finally, chemical measurements may include capnography (measure of $CO_2$ in exhaled gasses), measures of venous blood or heart tissue oxygenation, etc.

It will be appreciated by those of ordinary skill in the art that the various electrical, physical and chemical measurements may be taken by or input to the defibrillator using a variety of external or invasive sensors incorporated in the defibrillator and well known to those of ordinary skill in the art. As for those measurements relating to cardiac motion and size, those of ordinary skill in the art will recognize that such measurements may be provided by ultrasound as well.

Cardiac Motion: Ultrasound may be used to estimate the size of the heart chambers as well as an indication of wall motion during ventricular fibrillation. Other motion detectors might be of use such as microwave detectors. Even impedance imaging might give an estimate of heart size and this might be done from either defibrillation pads of from ECG patches on the patient.

Once the viability index is determined using any of the techniques described above alone or in combination, it is then used to determine whether the first treatment waveform described above is delivered to the patient. For example, in one embodiment of the present invention, the viability index is then compared against a predetermined numerical threshold or "viability threshold" that quantifies a minimum threshold of viability for a human heart, depending on what factors are used to measure viability, and thus, the likelihood of PEA. The viability threshold is selected as a basis for a decision by the device on whether or not the pretreatment waveform will be delivered prior to the defibrillation waveform. If the viability index is greater than the viability threshold, the patient would receive the defibrillation waveform only. If the viability index is less than the viability threshold, then the patient would receive both the pretreatment waveform and then the defibrillation waveform.

For example, if the likelihood of PEA is being assessed as a function of the duration of ventricular fibrillation, then the viability index may take the form of the mathematical inverse of the duration that the patient has been in ventricular fibrillation (i.e., 1/duration) and the viability threshold may correspond to the inverse of a predetermined maximum duration of ventricular fibrillation for which a human heart is still considered viable and unlikely to go into PEA when shocked. Accordingly, if the viability index for duration is less than the viability threshold for duration, then the patient would receive PEA electrotherapy, i.e., both the pretreatment waveform and the defibrillation waveform. Also, the magnitude of the pretreatment waveform can be adjusted to deliver greater energy when the likelihood of PEA is high. For example, the duration, amplitude, and/or frequency of the pretreatment waveform can be increased when the viability index for the subject is low.

All of the techniques described above for determining the likelihood of PEA can be implemented by the signal analyzer 122 and/or controller 121 of the apparatus of FIG. 5 as implemented in hardware and/or software. Electrical activity from the heart of the patient can be detected through the same electrodes used to defibrillate the heart, or through different electrodes. Further, if the external defibrillator is a manual defibrillator or an AED placed in manual mode, delivery of the first treatment waveform may be manually initiated by the operator rather than automatically initiated by the device. For example, the user interface 124 may be configured to report an indicia of the viability index to the operator, e.g., via a text or voice prompt of the index itself or via a "PEA therapy advised" prompt. Based on the indicia, the operator may then manually enable the defibrillator to deliver the first treatment waveform.

In another embodiment of the invention, the controller of the external defibrillator is configured so that the system provides a single defibrillation waveform upon first administration of a waveform to the patient (i.e., a waveform corresponding to the "second" waveform referred to herein), and then—if the first waveform does not restore organized electrical activity to the heart—a second defibrillation sequence is administered to a patient during the same therapeutic session, which second defibrillation sequence implements a defibrillation sequence comprised of a first and second waveform as described herein.

Numerous additional features may be included in the external defibrillator, including but not limited to self-test circuitry, circuitry and an associated speaker for generating audible voice prompts to the operator, watch-dog timers, shock energy reducers (for reducing the magnitude of the delivered shock for smaller patients such as pediatric patients) data recorders and ECG filters and amplifiers, and circuitry and memory storage devices for the archival storage and retrieval of rescue information, The present invention is explained in greater detail in the following non-limiting examples.

EXAMPLE 1

Animal preparation. Mixed breed pigs of either sex, weighing about 30–40 kg were anesthetized with telazol (4.4 mg/kg), xylazine (2.2 mg/kg), and atropine (0.04 mg/kg) injected IM and maintained with isoflurane. Lactated Ringer's solution was administered IV at a rate of 5–10 ml/kg/hr throughout the experiment via a peripheral vein (femoral or external jugular). The pigs were intubated and mechanically ventilated to maintain pH and $PaCO_2$ with the normal range. The right and left lateral aspect of the thorax were shaved for application of self-adhesive defibrillation electrodes.

The pig was placed in dorsal recumbancy. A high fidelity pressure catheter was placed into a femoral artery for continuous measurement of blood pressure. A second high fidelity catheter was placed in the left ventricle. A pacing catheter was placed in the right ventricle. Location of the catheters was confirmed by fluoroscopy.

Succinylcholine drip was given to provide skeletal muscle relaxation prior to the first electrical pulse. Anesthesia was kept at the same level of 2% isoflurane during the study, to the extent that was possible to maintain the animal at stage II, plane 2–3 anesthesia.

Procedure. Data collection included surface lead II ECG, systemic arterial pressure, LV pressure, and a trace showing the delivery of electrical pulses. This data was collected using a computerized data acquisition system. Pulse packet therapy was delivered to the defibrillation electrodes on the body surface of the animal from an arbitrary waveform linear amplifier. The size, shape and timing of the pulses were controlled by a digital waveform generator.

Determine the effect of varying electrical pulses delivered to the body surface on blood pressure, HR, and LV pressure. The effect of 3 different pulse trains and varying current strength delivered from defibrillation patches on HR, blood pressure, and LV pressure was determined. The total pulse train duration, or duty cycle, was 10 ms. The duty cycle was 2.0 ms on and 8.0 ms pulse off, 1.0 ms on and 9.0 msoff, or 0.5 ms on and 9.5 ms off. Pulses were delivered 3 times in 80 ms synchronized to begin with the R wave. A noncumulative strength-response curve was generated for the change from baseline in systolic BP, systolic LV pressure, and HR. The current delivered was 2.5, 5, 10, and 15 Amps. The on/off duty cycle and the amount of current delivered was delivered in random order as determined by a "random number" generator. Two minutes elapse between each episode of pulse therapy.

Determine the effect of external pulse therapy at 0 (no pulse therapy), 5, 10 & 15 Amps and at 3 different duty cycles on SAP and LV pressure for electrically-induced VF of 20 sec duration compared to SAP and LV pressure without pulse therapy preceding the defibrillation shock. VF proceeded for 10 s, and then pulse therapy was delivered over approximately 10 more s prior to delivery of a defibrillation shock at 1.5 times the DFT. Each episode of electrical VF was separated by 4 min.

Effect of 5, 10 & 15 Amp pulse strength delivered prior to shock on SAP & LV pressure: Electrical VF is induced and a defibrillation shock is delivered at 1.5 times the electrical DFT determined earlier in the experiment. Prior to defibrillation, pulse therapy or no pulse therapy is delivered. No pulse therapy is delivered initially and after every therapy trials. The total pulse train duration, or duty cycle, is 10 ms. The duty cycle is 2.0 ms on and 8.0 ms pulse delay, 1.0 ms on and 9.0 ms off, or 0.5 ms on and 9.5 ms off. Pulse packets are delivered at 9, 6 and 3 seconds prior to the defibrillation shock. A noncumulative strength-response curve was is generated for the change from baseline in systolic BP, systolic LV pressure, and HR. The current delivered was 5, 10, and 15 Amps. The on/off duty cycle and the amount of current delivered was delivered in random order as determined by a "random number" generator. Four minutes elapse between each episode of VF. Thus, 13 episodes of VF & defibrillation (9 with pulse therapy & 4 without pulse therapy) occur in this portion of the study, and the combinations of the 2 variables (pulse therapy: 2.0 ms on & 8.0 ms off, 1.0 ms on & 9.0 ms off or 0.5 ms on and 9.5 ms off, and pulse strength: 5, 10 or 15 Amps) were randomized.

Figure 6:
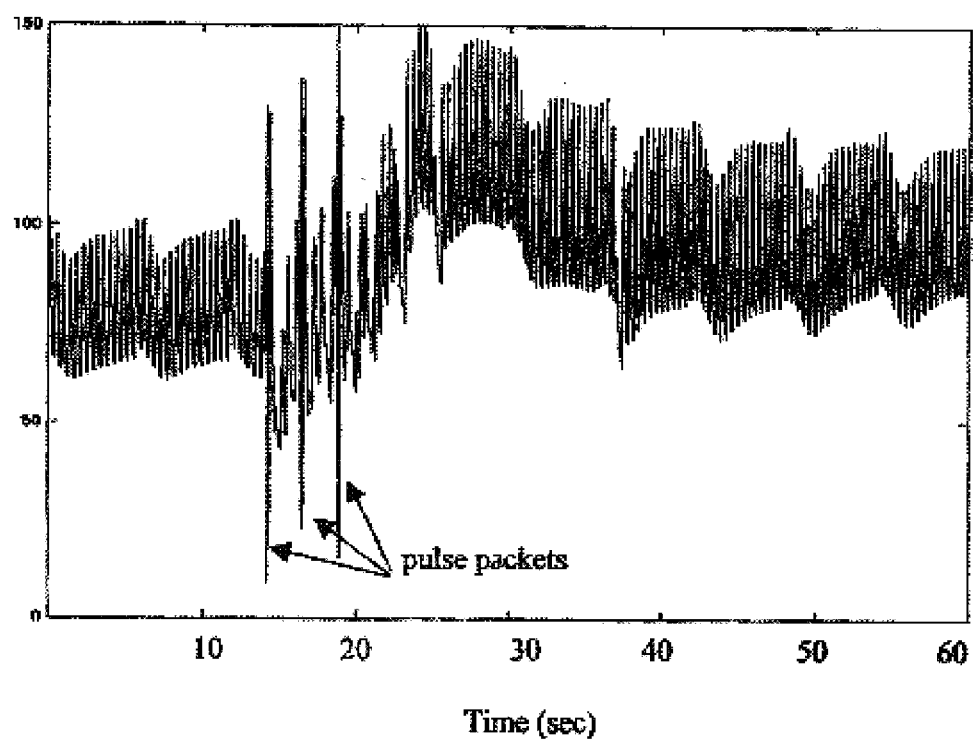
FIG. 6 shows, for comparative and background purposes, a tracing of arterial blood pressure (ABP) recorded while a series of pulse packets were delivered to the heart during normal sinus rhythm.

FIG. 6 shows, for background and comparative purposes, a tracing of arterial blood pressure (ABP) recorded while a series of pulse packets were delivered to the heart during normal sinus rhythm. The x-axis is time and the y-axis is ABP measured in mm of mercury (Hg). Each pulse packet contained nine 1-msec pulses spaced 10 msec. apart. Three sets of pulse packets were delivered. Each was timed to start 10-msec following the peak of the R-wave on the surface electrocardiogram. Five heartbeats occurred between each pulse packet. Sixty seconds of data is shown. Note that there is a rise in the ABP following the last pulse packet. Systolic ABP increases from approximately 100 mm Hg to 145 mm Hg over the 10 seconds following the final pulse packet. ABP slowly decreases but has not yet returned to baseline over the next 30 seconds.

Figure 7:
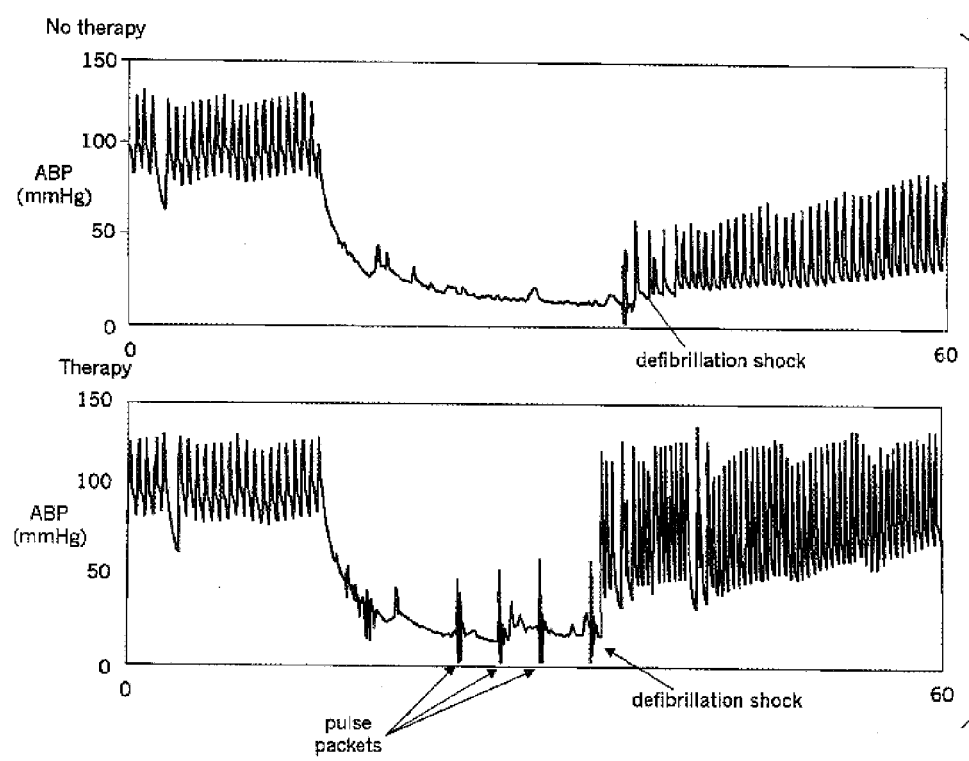
FIG. 7 shows the effect of the pulse therapy when delivered during VF.

FIG. 7 shows the effect of the pulse therapy when delivered during VF. The two panels show arterial blood pressure (ABP) measured in mm. Hg. The top panel shows the ABP time course following 20 seconds of VF. The systolic blood pressure is approximately 40% of baseline immediately following the delivery of a successful defibrillation shock. The systolic blood pressure slowly rises following the shock but has not reached baseline at 25 seconds following the shock. The bottom panel again shows the ABP time course following 20 seconds of VF but this time 3 pulse packets were delivered during VF. Each pulse packet contained nine 1-msec pulses spaced 10 msec. apart. Three sets of pulse packets were delivered. The time between each pulse packet was 3 seconds. The systolic blood pressure is almost the same as at baseline just before VF initiation immediately following the delivery of a successful defibrillation shock.

Figure 8:
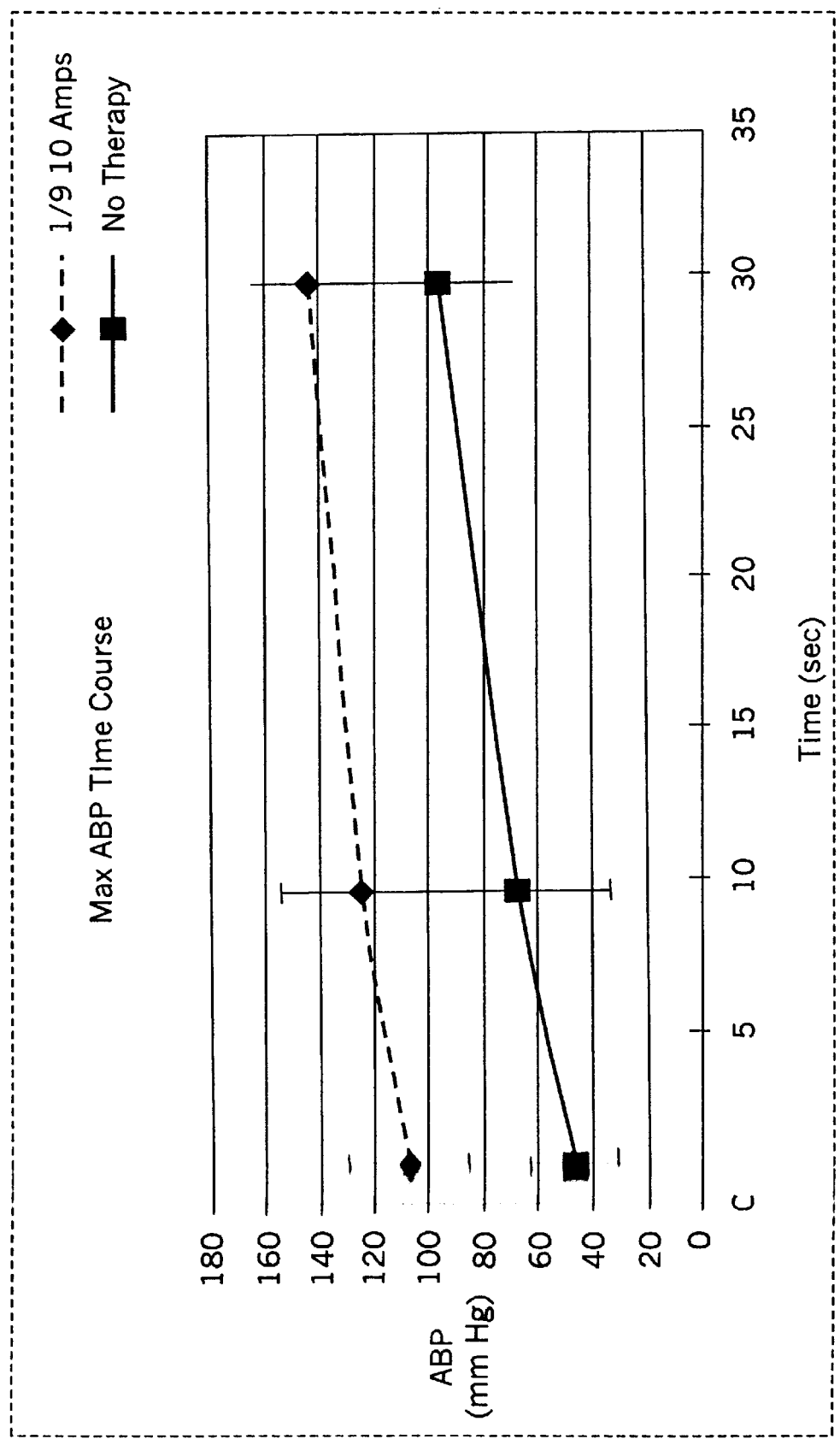
FIG. 8 shows the time course of recovery of ABP following successful defibrillation.

FIG. 8 shows the time course of recovery of ABP following successful defibrillation (occurring at time 0 on the X axis). The solid line represents the average systolic blood pressure following the shock without any pulse therapy in 6 animals. The dashed line represents the average systolic blood pressure in the same 6 animals after three packets of pulse therapy and successful defibrillation. Each packet consisted of nine 10 Amp 1-msec pulses each separated by 10 msec. Systolic blood pressure was higher for therapy compared with no therapy at all three time points examined.

Figure 9:
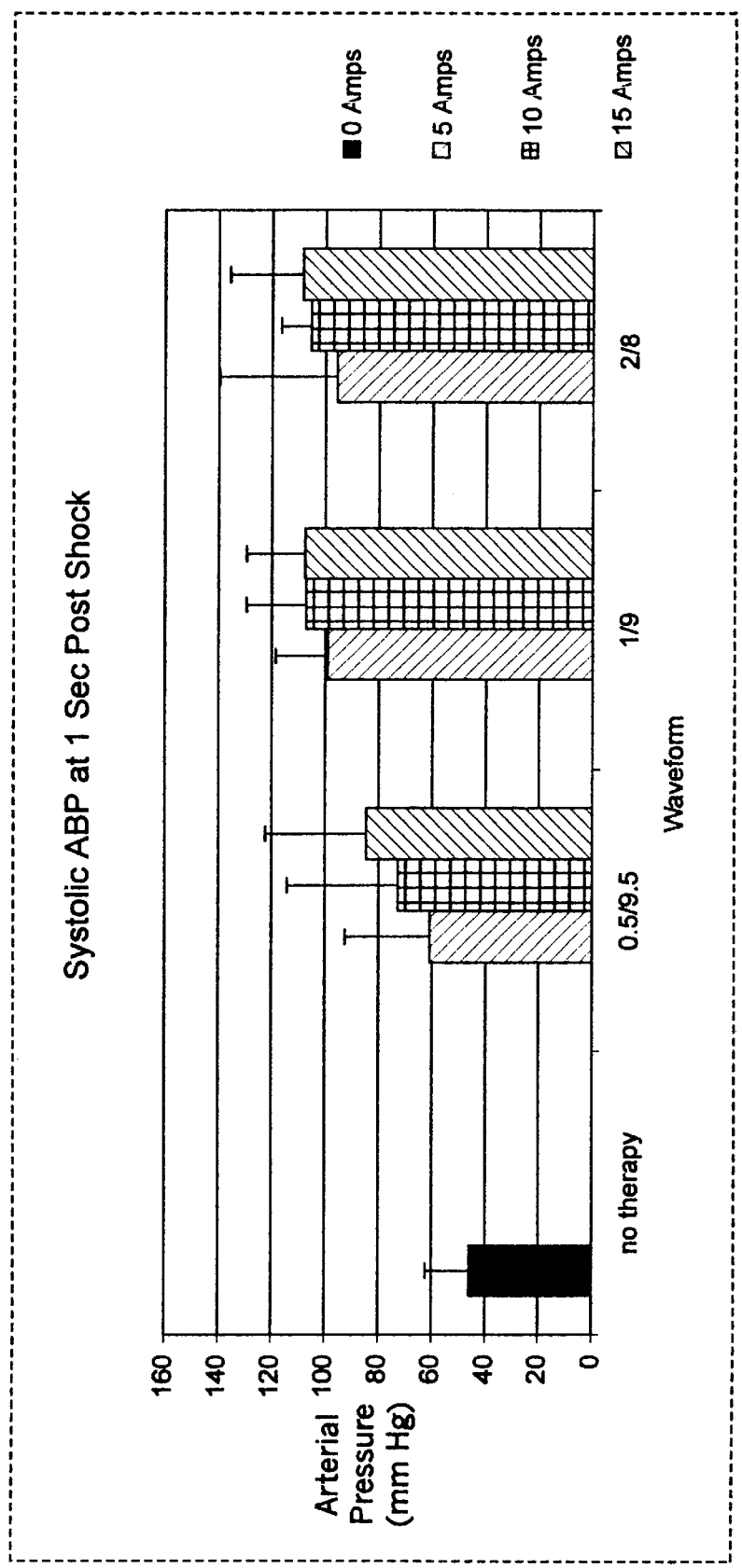
FIG. 9 shows the effect of changing packet pulse duration and strength. Pulse durations tested were 0.5 msec, 1 msec, and 2 msec.

FIG. 9 shows the effect of changing packet pulse duration and strength. Pulse durations tested were 0.5 msec, 1 msec, and 2 msec. Pulse strengths tested were 5, 10, and 15 Amps. Compared to no therapy, all pulse strengths increased systolic blood pressure at 1 second following the shock. As the pulse strength and duration increased, so did systolic blood pressure.

EXAMPLE 2

This example demonstrates that a burst of 15–30 1-msec pulses delivered during ventricular fibrillation can increase heart rate, arterial pressure and LV pressure following defibrillation. Beta blockade prevents most of this post-shock increase in heart rate and hemodynamics.

Ten pigs, 25–30 kgs, were premedicated with Telazol, 4.4 mg/kg, xylazine, 2.2 mg/kg and atropine, 0.04 mg/kg. Animals were intubated with a cuffed endotracheal tube and were ventilated at a rate of 10–15 ml/kg/min. Anesthesia was maintained using 1–3% isoflurane. A 7-Fr hemostatic sheath was placed in the left femoral artery and an 8-Fr hemostatic sheaths were placed in the right femoral artery and left jugular vein. Both the left and right jugular veins was isolated. An 8-Fr sheath was placed in the left jugular vein. A 5-Fr high fidelity pressure catheter (Millar Instruments) was advanced retrograde across the aortic valve into the left ventricle. A 3-Fr high fidelity pressure catheter was placed via a femoral sheath into the abdominal aorta. A transvenous defibrillation catheter was advanced into the right ventricular apex. A defibrillation can electrode was placed under the skin of the anterior left chest wall overlying the 2nd intercostal space. The distal defibrillation electrode was the anode for all burst stimulation and the first phase of the biphasic defibrillation shock. The proximal defibrillation catheter electrode connected to the can electrode served as the cathode.

A defibrillation threshold was determined using a three reversal up-down protocol using a log(0.1) Joule step size. (McDaniel, et al., *Med. Instrum.*, 21(3), 170–6 (June 1987). VF was induced using 60-Hz current applied to the right ventricular apex. Defibrillation shocks were delivered after 10 seconds of VF. An external cardiovertor-defibrillator (VENTAK ECD, Guidant Corp.) was used to deliver all defibrillation shocks. The defibrillator was triggered by a pulse generator (WPI). All subsequent defibrillation shocks were delivered at approximately 1.5× energy of the measured threshold. If a shock failed to defibrillate the heart, the trial was discarded and repeated.

The animal was challenged with 10 ug/kg/min of dobutamine for 4 minutes. Heart rate, blood pressure, and left ventricular pressure were recorded before and at the end of the dobutamine infusion. Following the dobutamine challenge, a 20 minute washout period was observed before any testing was performed.

Pulse Therapy. Prior to defibrillation shock delivery, a series of therapy pulses were delivered using a linear power amplifier (Guidant Corp.). Burst stimulation pulses were 1 msec in duration. Six pulse strengths were used: 0.1, 0.3, 1, 2, 5, and 10 Amps. Either 15 or 30 pulses were delivered. Time between pulses was 30 msec for 0.1 and 0.3 Amp pulses and 10 msec for all the rest. A 3 second delay was allowed between the burst therapy and the defibrillation shock. A total of 12 different pulses therapies was tested. Trial order was randomized across each animal. A control trial with no burst stimulation prior to defibrillation was performed before any burst therapy trials and after every 4th therapy trial.

Beta blockade. After the initial 16 burst stimulation and control trials, the animal was given timolol, 1 mg/kg. After 10 minutes, the dobutamine challenge was repeated. Following a 20 minute washout period for the dobutamine, the 12 burst therapy trials and 4 control trials were repeated.

At the end of the study, the animal was euthanized with KCl while still anesthetized. The heart was removed, weighed and examined grossly.

Data Collection and Analysis. Lead II ECG and the two pressure signals were collected with an 8-channel data acquisition system (Windaq, Dataq Co.) at a minimum sampling rate of 500 samples/sec. Data were analyzed using Matlab (Mathworks Co.). Values are given as the mean ± the standard deviation.

Repeated measures analysis of variance was used to compare mean values (SPSS, SPSS Inc.). A Student-Newman-Keuls post-hoc test was used to determine differences in individual means when the repeated measures analysis of variance showed a significant difference. A p-value<0.05 was considered significant.±

Results. Animal weight was 34±3 Kg. Heart weight was 160±20 gms. Mean defibrillation threshold was 488±55 Volts. Mean defibrillation shock strength delivered during pulse therapy testing was 732±89 Volts.

Figure 10:
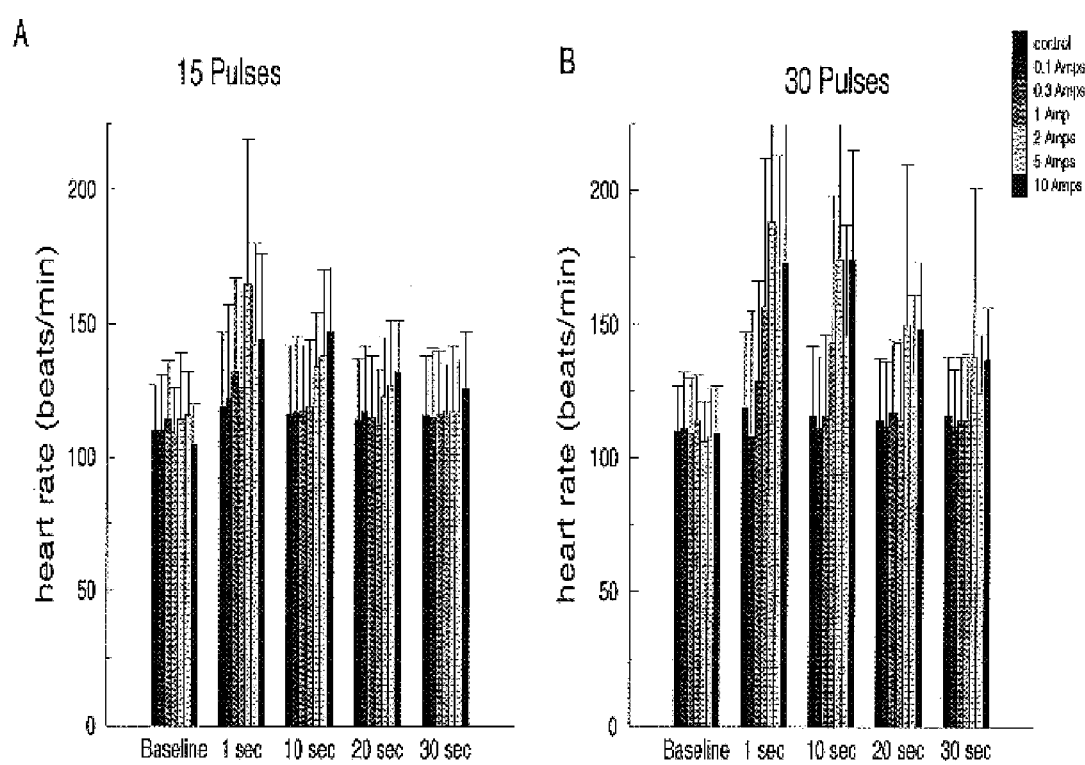
FIG. 10 shows the heart rate response to pulse therapy. Panel A: Heart rate following 15 pulses. Panel B: Heart rate following 30 pulses. Heart rate was significantly higher following 1, 2, 5, and 10 Amp pulse therapy than following defibrillation with no burst stimulation (control). There was no significant difference in heart rate following 15 therapy pulses compared to following 30 therapy pulses.

Control Pulses. For control shocks, heart rate did not change significantly over the 30 seconds following the shock from the baseline value of 110±17 beats per minute (FIG. 10). For shocks preceded by pulse therapy, heart rate was significantly higher following the 1, 2, 5 and 10 Amp pulses at 1, 10, and 20 seconds after the shock compared to baseline but was not different from baseline at 30 seconds. There was a trend towards a greater increase in heart rate with 30 pulses than with 15 pulses, but this difference did not reach significance.

Figure 11:
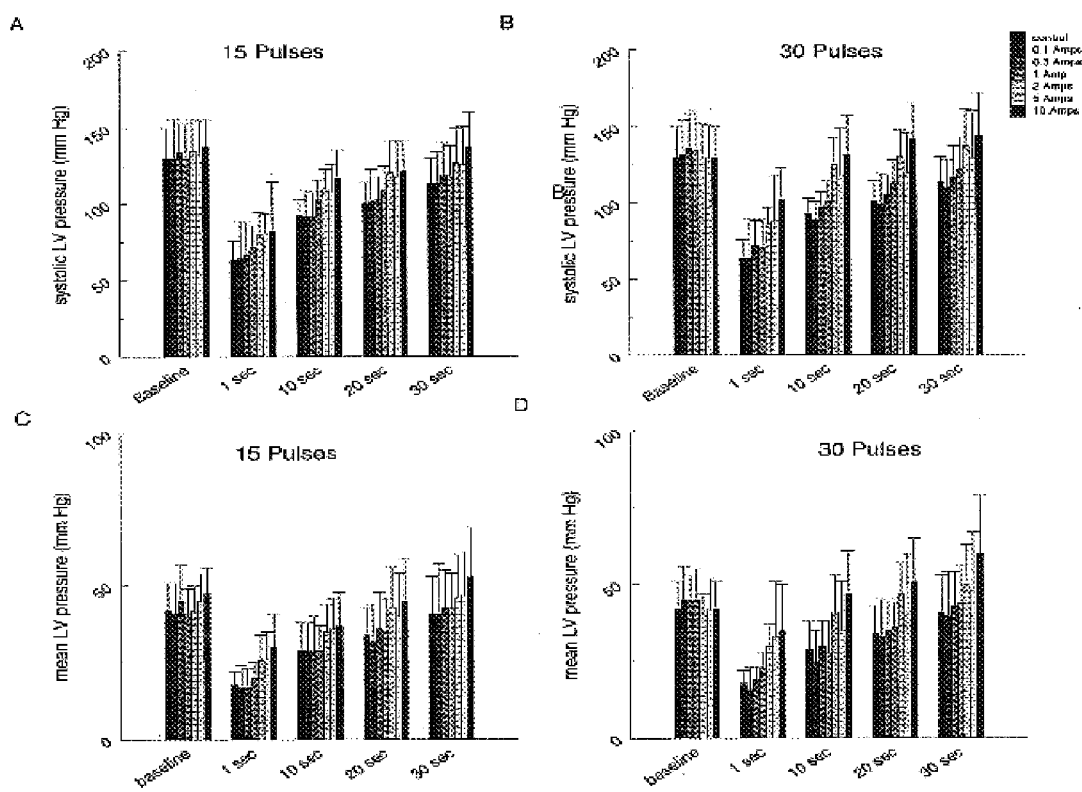
FIG. 11 shows the left ventricular pressure response to pulse therapy. Panel A: Systolic left ventricular pressure following 15 1-msec pulses. Panel B: Systolic left ventricular pressure following 30 1-msec pulses. Left ventricular systolic pressure was significantly higher for 2, 5, and 10 Amp pulses compared to that for control episodes. There was no significant difference between the response to 15 and 30 pulses. Panel C: Mean left ventricular pressure following 15 pulses. Panel D: Mean left ventricular pressure following 30 pulses. Left ventricular pressure was significantly higher for 2, 5 and 10 Amp pulses than for control episodes. There was no significantly difference between the response to 15 and 30 pulses.

For control shocks, systolic left ventricular pressure fell from 130±20 mmHg at baseline to 51±10 mmHg 1 second after the shock. By 30 seconds, systolic left ventricular pressure had increased to 91±12 mmHg, which was still significantly different than the baseline pressure (FIG. 11). For shocks with pulse therapy, systolic left ventricular pressure was significantly higher for pulse strengths of 2, 5, and 10 amps than for the control shocks. Thirty seconds after the shock, systolic left ventricular pressure was still significantly higher than for control shocks. Again there was a trend towards a greater increase in systolic left ventricular pressure for 30 than for 15 therapy pulses, but this did not reach significance.

For control shocks, left ventricular mean pressure dropped from 42±9 mmHg at baseline to 18±5 mmHg at 1 second following the shock. By 30 seconds, left ventricular mean pressure had increased to 41±12 mmHg (FIG. 11). Left ventricular mean pressure was significantly higher for either 15 or 30 pulses at pulse strengths of 2, 5, and 10 Amps than for control episodes. Thirty pulses did not significantly increase left ventricular mean pressure compared to 15 pulses.

Figure 12:
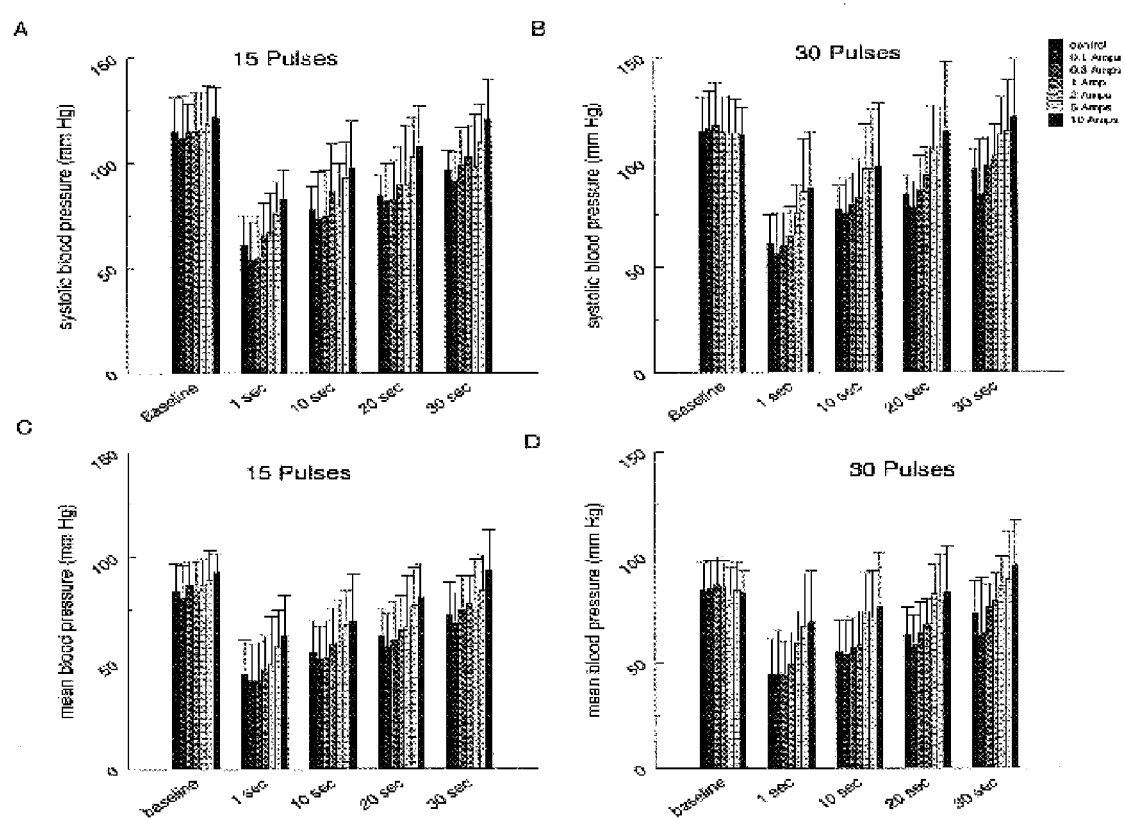
FIG. 12 shows the arterial pressure response to pulse therapy. Panel A: Systolic arterial pressure following 15 pulses. Panel B: Systolic arterial pressure following 30 pulses. Systolic arterial pressure was significant higher for 2, 5, and 10 Amp pulses than for control episodes. There was no significant difference between the response to 15 and 30 pulses. Panel C: Mean arterial pressure following 15 pulses. Panel D: Mean left ventricular pressure following 30 pulses. Mean arterial pressure was significantly higher for 5 and 10 Amp pulses than for control episodes. There was no significant difference between the response to 15 and 30 pulses.

For control shocks, systolic arterial pressure dropped from 115±17 mmHg at baseline to 51±14 mmHg one second following the shock. By 30 seconds, systolic arterial pressure had increased to 87±10 mmHg (FIG. 12). Systolic arterial blood pressure was significantly increased over baseline for 2, 5, and 10 Amp pulses. There was no significant difference in the systolic arterial pressure response to 15 and 30 pulses.

For control shocks, mean arterial pressure dropped from 84±14 mmHg to 45±16 mmHg at 1 second following the shock. By 30 seconds, mean arterial pressure had increased to 73±13 mmHg (FIG. 12). For shocks with pulse therapy, mean arterial blood pressure was significantly higher for either 15 or 30 pulses for pulse strengths of 5 and 10 amps than for control episodes at 1, 10, 20 and 30 seconds. There was no significant difference in the response of mean arterial pressure to 15 and 30 pulses.

Dobutamine test. Prior to any burst stimulation testing, dobutamine changed heart rate from 110±12 mmHg to 134±18 mmHg and systolic blood pressure from 112±24 mmHg to 158±24 mmHg (p<0.05). Following beta blocker administration, dobutamine changed heart rate from 107±17 mmHg to 111±17 mmHg and systolic blood pressure from 106±18 mmHg to 113±22 mmHg (p=NS).

Pulses during Beta Blockade. Beta blockade caused a significant decrease in heart rate from 110±17 to 107±12 mmHg. Systolic blood pressure was lowered from 115±17 to 100±19 mmHg, and mean arterial blood pressure was lowered from 86±13 to 70±15 mmHg. Systolic LV pressure was lowered from 132±21 to 116±16 mmHg and mean LV pressure was lowered from 43±9 to 36±8 mmHg. All of these changes were significant.

Figure 13:
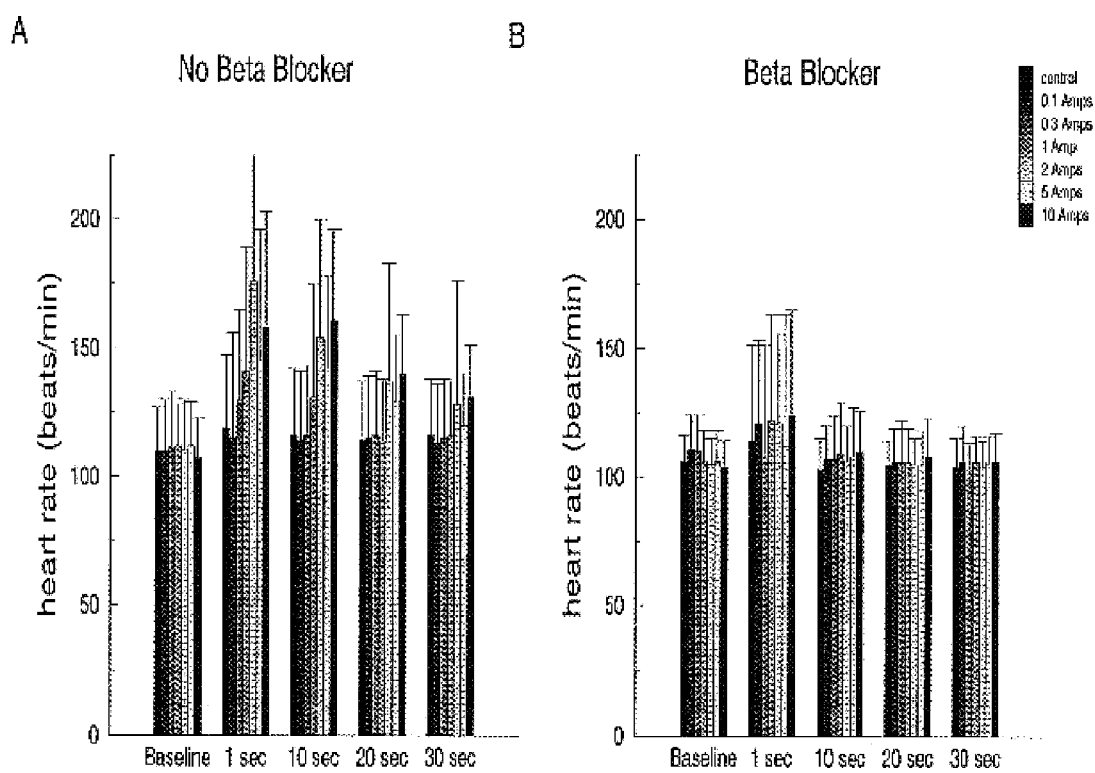
FIG. 13 shows the heart rate response to pulse therapy without (Panel A) and with beta blockade (Panel B). The 15 and 30 pulse results have been combined. Heart rate response did not change significantly with delivery of pulses before the shock with beta blockade as it did for the 1–10 Amp pulses without beta blockade.

After beta blockade, heart rate 1, 10, 20, or 30 seconds following defibrillation for control episodes did not change significantly from the 110±17 beats per minute value before fibrillation induction (baseline) 1, 10, 20, or 30 seconds following the shock. None of the pulse therapy changed heart rate from the control values (FIG. 13).

Figure 14:
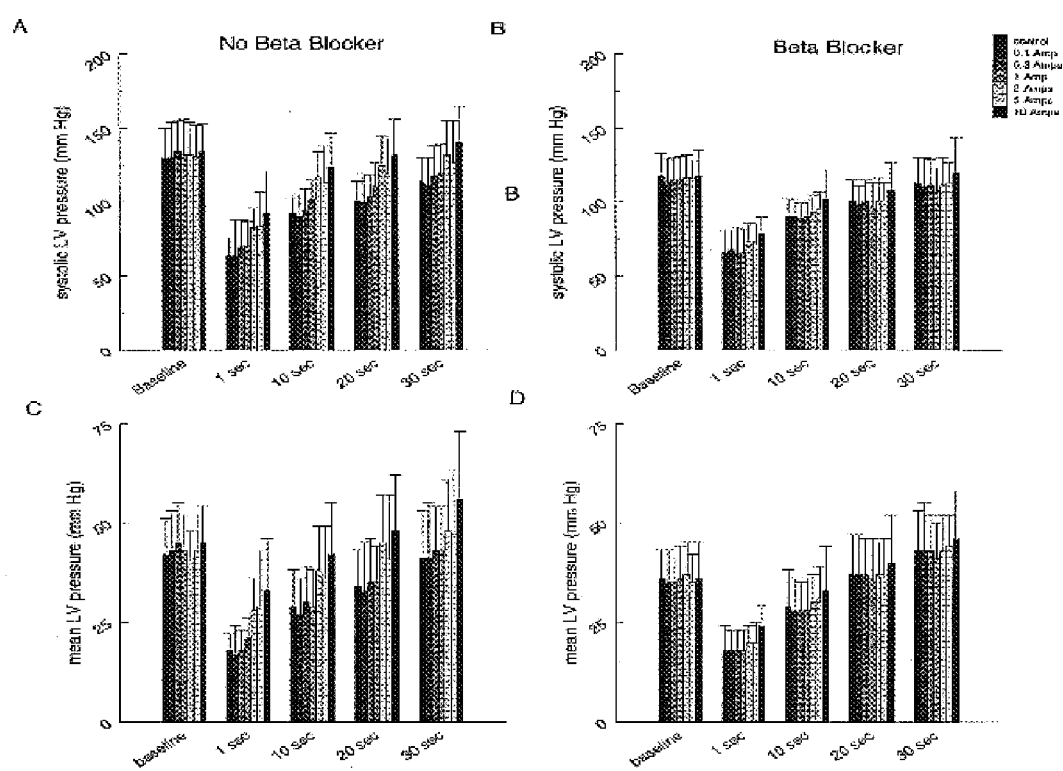
FIG. 14 shows the systolic left ventricular pressure response to pulse therapy without (Panel A) and with beta blockade (Panel B). The 15 and 30 pulse results have been combined. Only the response to the 10 Amp pulses was significantly higher than that for control episodes. Mean left ventricular pressure response to pulse therapy without beta blockade (Panel C) and with beta blockade (Panel D). Mean left ventricular pressure did not change significantly with delivery of pulses before the shock with beta blockade.

For control episodes, systolic left ventricular pressure dropped from a baseline of 116±16 mmHg to 66± mmHg 1 second following the shock. By 30 seconds, systolic left ventricular pressure had increased to 113±17 mmHg (FIG. 14). Only the 10 Amp pulses increased systolic left ventricular pressure above control shock values. There was no significant difference in the response to 15 and 30 pulses.

For control episodes, mean left ventricular pressure dropped from a baseline value of 42±9 mmHg to 33±10 1 second following the shock. By 30 seconds, mean left ventricular pressure had increased to 38±10 mmHg (FIG. 14). None of the pulse therapies changed mean left ventricular pressure significantly differently than for control episodes.

Figure 15:
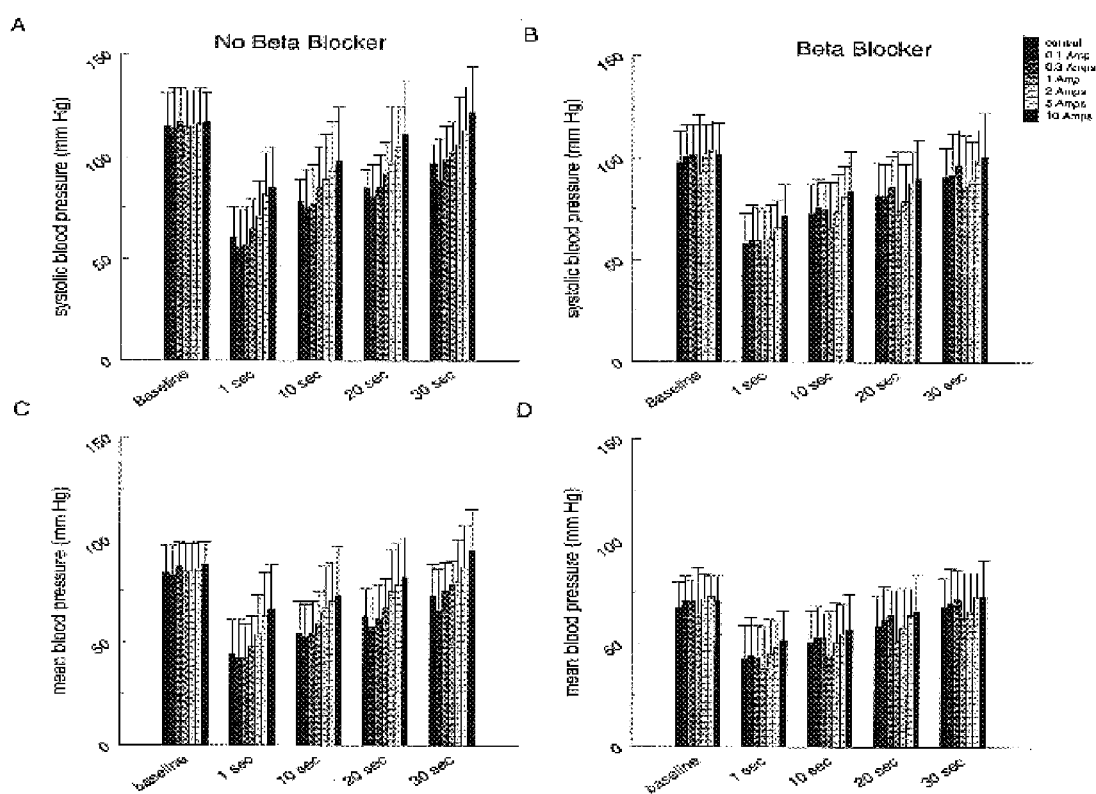
FIG. 15 shows the systolic arterial pressure response to pulse therapy without (Panel A) and with beta blockade (Panel B). Mean arterial pressure response to pulse therapy without beta blockade (Panel C) and with beta blockade (Panel D). The 15 and 30 pulse results have been combined. Neither systolic or mean arterial pressure changed significantly with delivery of pulses before the shock with beta blockade.

For control episodes, systolic arterial pressure dropped from 98±15 mmHg at baseline to 58±15 mmHg 1 second after the shock. By 30 seconds, systolic blood pressure had returned to 98±15 mmHg (FIG. 15). None of the pulse therapies changed systolic arterial pressure significantly differently than for control episodes.

For control episodes, mean arterial pressure decreased from 84±13 to 45±16 mmHg 1 second following the shock. By 30 seconds following the shock, mean arterial pressure had returned to 73±15 mmHg (FIG. 15). None of the pulse therapies changed mean arterial pressure significantly from the control episode values.

The findings of this example are two-fold. First, pulse stimulation that is too weak to defibrillate, when given during ventricular fibrillation prior to the defibrillation shock increases heart rate, arterial pressure and left ventricular pressure following successful defibrillation compared to that following defibrillation without prior stimulation. Second, the effect on post-shock cardiac hemodynamics can be blocked by beta blockers, suggesting that the pulses delivered during ventricular fibrillation stimulate the sympathetic nervous system.

There are at least two conditions that could particularly benefit from improved hemodynamics following a defibrillation shock. First, in heart failure patients with an implantable cardiovertor-defibrillator, the combination of pre-existing hemodynamic compromise and the compromise caused by the arrhythmia itself may push the patient to a point where their heart can no longer pump enough blood. Second, in sudden cardiac arrest victims in whom ventricular fibrillation has lasted for several minutes, heart function following defibrillation may be severely compromised. Pulse therapy should be effective in improving hemodynamics in both of these situations.

The foregoing is illustrative of the present invention, and is not to be construed as limiting thereof. The invention is defined by the following claims, with equivalents of the claims to be included therein.

We claim:

1. A method of reducing the likelihood of onset of pulseless electrical activity after defibrillation in a subject afflicted with a fibrillating heart, said method comprising the steps of:
   administering to a subject afflicted with fibrillation a first treatment waveform, said first treatment waveform insufficient to defibrillate said heart; and then
   administering to said subject a second treatment waveform that defibrillates said heart and restores organized electrical activity in said heart;
   with said first treatment waveform reducing the likelihood of onset of pulseless electrical activity following said second treatment waveform as compared to that likelihood which would be present in the absence of said first treatment waveform.

2. A method according to claim 1, wherein said fibrillation is ventricular fibrillation.

3. A method according to claim 1, wherein said first treatment waveform comprises a single electrical pulse.

4. A method according to claim 1, wherein said first treatment waveform comprises a series of electrical pulses.

5. A method according to claim 1, wherein said first treatment waveform is insufficient to reduce the defibrillation threshold of said subject.

6. A method according to claim 1, wherein said second treatment waveform comprises a single electrical pulse.

7. A method according to claim 1, wherein said second treatment waveform comprises a series of electrical pulses.

8. A method according to claim 1, wherein said first treatment waveform is administered by external electrodes and has an energy of from about 1 to 400 Joules.

9. A method according to claim 1, wherein said first treatment waveform is administered by internal electrodes and has an energy of from about 0.1 to 50 Joules.

10. A method according to claim 1, wherein said first treatment waveform and said second treatment waveform are sequential.

11. A method according to claim 1, wherein said second treatment waveform immediately follows said first treatment waveform.

12. A method according to claim 1, wherein said second treatment waveform follows said first treatment waveform by from 1 millisecond to 10 seconds.

13. A method according to claim 1, wherein said first treatment waveform and said second treatment waveform are at least partially interleaved.

14. A method according to claim 1, wherein said first treatment waveform is delivered through the same set of electrodes as said second treatment waveform.

15. A method according to claim 1, wherein said first treatment waveform is delivered through a different set of electrodes as said second treatment waveform.

16. A method according to claim 1, wherein said first treatment waveform is delivered by at least one cutaneous electrode.

17. A method according to claim 1, wherein said first treatment waveform is delivered by at least one subcutaneous electrode.

18. A method according to claim 1, wherein said first treatment waveform is delivered by at least one epicardial electrode.

19. A method according to claim 1, wherein said first treatment waveform is delivered by at least one transvenous electrode.

20. A method according to claim 1, wherein said first treatment waveform is delivered by at least one transvenous coronary sinus electrode positioned in the coronary sinus or a cardiac vein.

21. A system for the defibrillation of the heart of a patient in need of such treatment, which system provides reduced likelihood of onset of pulseless electrical activity after defibrillation in a subject afflicted with a fibrillating heart, said system comprising:
   a power supply; and
   a controller operatively associated with said power supply, said controller configured for delivering a defibrillation sequence comprising a first treatment waveform, said first treatment waveform insufficient to defibrillate said heart; and then a second treatment waveform that defibrillates said heart and restores organized electrical activity in said heart;
   with said first treatment waveform reducing the likelihood of onset of pulseless electrical activity following said second treatment waveform as compared to that likelihood which would be present in the absence of said first treatment waveform.

22. A system according to claim 21, wherein said fibrillation is ventricular fibrillation.

23. A system method according to claim 21, wherein said first treatment waveform comprises a single electrical pulse.

24. A system according to claim 21, wherein said first treatment waveform comprises a series of electrical pulses.

25. A system according to claim 21, wherein said first treatment waveform is insufficient to reduce the defibrillation threshold of said subject.

26. A system according to claim 21, wherein said second treatment waveform comprises a single electrical pulse.

27. A system according to claim 21, wherein said second treatment waveform comprises a series of electrical pulses.

28. A system according to claim 21, further comprising:
a plurality of external electrodes operatively associated with said controller,
and wherein said first treatment waveform is administered by external electrodes and has an energy of from about 1 to 400 Joules.

29. A system according to claim 21, further comprising:
a plurality of internal electrodes operatively associated with said controller;
and wherein said first treatment waveform is administered by internal electrodes and has an energy of from about 0.1 to 50 Joules.

30. A system according to claim 21, wherein said controller is configured so that said first treatment waveform and said second treatment waveform are sequential.

31. A system according to claim 21, wherein said controller is configured so that said second treatment waveform immediately follows said first treatment waveform.

32. A system according to claim 21, wherein said controller is configured so that said second treatment waveform follows said first treatment waveform by from 1 millisecond to 10 seconds.

33. A system according to claim 21, wherein said controller is configured so that said first treatment waveform and said second treatment waveform are at least partially interleaved.

34. A system according to claim 21, wherein said controller is configured so that said first treatment waveform is delivered through the same set of electrodes as said second treatment waveform.

35. A system according to claim 21, wherein said controller is configured so that said first treatment waveform is delivered through a different set of electrodes as said second treatment waveform.

36. A system according to claim 21, further comprising at least one cutaneous electrode operatively associated with said controller, and wherein said controller is configured so that said first treatment waveform is delivered by said at least one cutaneous electrode.

37. A system according to claim 21, further comprising at least one subcutaneous electrode operatively associated with said controller, and wherein said first treatment waveform is delivered by said at least one subcutaneous electrode.

38. A system according to claim 21, futher comprising at least one epicardial electrode operatively associated with said controller, and wherein said first treatment waveform is delivered by at least one epicardial electrode.

39. system according to claim 21, further comprising at least one transveneous electrode operatively associated with said controller, and wherein said first treatment waveform is delivered by said at least one transveneous electrode.

40. A system according to claim 21, further comprising at least one transveneous coronary sinus electrode operatively associated with said controller, and wherein said first treatment waveform is delivered by said at least one transveneous coronary sinus electrode.

41. A method for the external defibrillation of the heart of a patient afflicted with ventricular fibrillation, comprising the steps of:
externally administering to said patient a first treatment waveform, said first treatment waveform insufficient to defibrillate said heart; and then
externally administering to said subject a second treatment waveform that defibrillates said heart and restores organized electrical activity in said heart;
wherein said first treatment waveform has an energy of from about 1 to about 400 Joules.

42. A method according to claim 41, wherein:
said first treatment waveform is administered for a time of 0.05 to 10 seconds; and
said second treatment waveform is administered within 5 seconds of said first treatment waveform.

43. A method according to claim 41, further comprising the steps of:
optionally generating a warning signal prior to said first treatment waveform; then
generating a warning signal during said first treatment waveform, and then
optionally generating a warning signal during said second treatment waveform.

44. A method according to claim 43, wherein said warning signal comprises an auditory, visual, or tactile signal.

45. A method according to claim 43, wherein said step of externally administering to said patient a first treatment waveform is preceded by the step of:
determining the presence or absence of a likelihood of pulseless electrical activity following defibrillation, and wherein:
said step of administering said first treatment waveform is carried out if a likelihood of pulseless electrical activity following defibrillation is determined, and said step of administering said first treatment waveform is eliminated if a likelihood of pulseless electrical activity following defibrillation is not determined.

46. A method according to claim 41, wherein said second treatment waveform has an energy of from about 100 to 400 Joules.

47. A method according to claim 41, wherein said first treatment waveform and said second treatment waveform are sequential.

48. A method according to claim 41, wherein said second treatment waveform immediately follows said first treatment waveform.

49. A method according to claim 41, wherein said first treatment waveform and said second treatment waveform are at least partially interleaved.

50. An external defibrillation system for the external defibrillation of the heart of a patient afflicted with ventricular fibrillation, comprising:
a power supply; and
a controller operatively associated with said power supply, said controller configured for delivering a defibrillation sequence comprising a first treatment waveform, said first treatment waveform insufficient to defibrillate said heart and having an energy from about 1 to 400 Joules; and then a second treatment waveform that defibrillates said heart and restores organized electrical activity in said heart.

51. A system according to claim 50, said controller configured so that
said first treatment waveform is administered for a time of 0.05 to 10 seconds; and
said second treatment waveform is administered within 5 seconds of said first treatment waveform.

52. A system according to claim 50, further comprising a warning signal generator operatively associated with said controller, and with said controller configured to:
optionally generating a warning signal prior to said first treatment waveform; then
generating a warning signal during said first treatment waveform, and then
optionally generating a warning signal during said second treatment waveform.

53. A system according to claim 52, wherein said warning signal generator is an auditory, visual, or tactile signal generator.

54. A system according to claim 52, further comprising means for determining the likelihood of pulseless electrical activity following defibrillation configured so that said step of administering said first treatment waveform is carried out if a likelihood of pulseless electrical activity following defibrillation is determined, and said step of administering said first treatment waveform is eliminated if a likelihood of pulseless electrical activity following defibrillation is not determined.

55. A system according to claim 50, wherein said controller is configured so that said second treatment waveform has an energy of from about 100 to 400 Joules.

56. A system according to claim 50, wherein said controller is configured so that said first treatment waveform and said second treatment waveform are sequential.

57. A system according to claim 50, wherein said controller is configured so that said second treatment waveform immediately follows said first treatment waveform.

58. A system according to claim 50, wherein said controller is configured so that said first treatment waveform and said second treatment waveform are at least partially interleaved.

59. A method of reducing the likelihood of onset of pulseless electrical activity after defibrillation with an implantable defibrillator in a subject afflicted with a fibrillating heart, said method comprising the steps of:
administering to a subject afflicted with fibrillation a first treatment waveform, said first treatment waveform insufficient to defibrillate said heart; and then
administering to said subject a second treatment waveform that defibrillates said heart and restores organized electrical activity in said heart;
with said first treatment waveform reducing the likelihood of onset of pulseless electrical activity following said second treatment waveform as compared to that likelihood which would be present in the absence of said first treatment waveform.

60. A method according to claim 59, wherein at least one of said first and second treatment waveforms is delivered by an electrode positioned in the coronary sinus, in a vein on the surface of the left ventricle, or in a vein at the junction of the right and left ventricles.

61. A method according to claim 59, wherein at least one of said first and second treatment waveforms is delivered by an electrode positioned on an external surface portion of said implantable defibrillator.

62. A method according to claim 59, wherein said first treatment waveform is delivered between at least a first electrode and second electrode;
said first electrode selected from the group consisting of right ventricle, superior vena cava, and right atrium electrodes; and
said second electrode selected from the group consisting of thoracic, superior vena cava, left ventricle, coronary sinus, left ventricle vein electrodes and left and right ventricle junction vein electrodes.

63. A method according to claim 59, wherein said second treatment waveform is delivered between at least a first electrode and second electrode;
said first electrode selected from the group consisting of right ventricle, superior vena cava, and right atrium electrodes; and
said second electrode selected from the group consisting of thoracic, superior vena cava, left ventricle, coronary sinus, left ventricle vein electrodes, and left and right ventricle junction electrodes.

64. A method according to claim 59, wherein said first treatment waveform has an energy of from about 0.1 to 50 Joules.

65. A method according to claim 59, wherein said second treatment waveform has an energy of from about 1 to 50 Joules.

66. A method according to claim 59, wherein said first treatment waveform and said second treatment waveform are sequential.

67. A method according to claim 59, wherein said second treatment waveform immediately follows said first treatment waveform.

68. A method according to claim 59, wherein said first treatment waveform and said second treatment waveform are at least partially interleaved.

69. An implantable defibrillator for defibrillating the heart of a subject in need therof, comprising:
a power supply; and
a controller operatively associated with said power supply, said controller configured for delivering a defibrillation sequence comprising a first treatment waveform, said first treatment waveform insufficient to defibrillate said heart; and then a second treatment waveform that defibrillates said heart and restores organized electrical activity in said heart; with said first treatment waveform reducing the likelihood of onset of pulseless electrical activity following said second treatment waveform as compared to that likelihood which would be present in the absence of said first treatment waveform.

70. A system according to claim 69, further comprising an electrode configured for positioning in the coronary sinus or in a vein on the surface of the left ventricle of said heart, wherein at least one of said first and second treatment waveforms is delivered by said electrode.

71. A system according to claim 69, further comprising an electrode positioned on an external surface portion of said implantable defibrillator, wherein at least one of said first and second treatment waveforms is delivered by said electrode.

72. A system according to claim 69, further comprising at least a first electrode and a second electrode, and wherein said controller is configured so that said first treatment waveform is delivered between said first electrode and second electrode;
said first electrode selected from the group consisting of right ventricle, superior vena cava, and right atrium electrodes; and said second electrode selected from the group consisting of thoracic, superior vena cava, left ventricle, coronary sinus, left ventricle vein electrodes, and left and right ventricle junction vein electrodes.

73. A system according to claim 69, further comprising at least a first electrode and a second electrode, and wherein said controller is configured so that said second treatment waveform is delivered between said first electrode and second electrode;

said first electrode selected from the group consisting of right ventricle, superior vena cava, and right atrium electrodes; and said second electrode selected from the group consisting of thoracic, superior vena cava, left ventricle, coronary sinus, left ventricle vein electrodes, and left and right ventricle junction vein electrodes.

74. A system according to claim 69, said controller configured so that said first treatment waveform has an energy of from about 0.1 to 50 Joules.

75. A system according to claim 69, said controller configured so that said second treatment waveform has an energy of from about 1 to 50 Joules.

76. A system according to claim 69, said controller configured so that said first treatment waveform and said second treatment waveform are sequential.

77. A system according to claim 69, said controller configured so that said second treatment waveform immediately follows said first treatment waveform.

78. A system according to claim 69, said controller configured so that said first treatment waveform and said second treatment waveform are at least partially interleaved.

79. A defibrillation system for the defibrillation of the heart of a patient afflicted with ventricular fibrillation, comprising:

a detector for detecting electrical activity from the heart of said patient during ventricular fibrillation;

a power supply;

a signal analyzer for determining the likelihood of pulseless electrical activity in said patient after delivery of a defibrillation treatment waveform to said patient; and a controller operatively associated with said detector, said power supply and said signal analyzer, said controller configured for delivering a defibrillation sequence, said defibrillation sequence optionally comprising a first treatment waveform, said first treatment waveform insufficient to defibrillate said heart, and then delivering a second treatment waveform that defibrillates said heart and restores organized electrical activity in said heart;

and wherein said first treatment waveform is delivered when a high likelihood of pulseless electrical activity after defibrillation is determined, and said first treatment waveform is not delivered when a low likelihood of pulseless electrical activity after defibrillation is determined.

80. A system according to claim 79, said controller configured so that said first treatment waveform is administered for a time of 0.05 to 10 seconds; and said second treatment waveform is administered within 5 seconds of said first treatment waveform.

81. A system according to claim 79, further comprising a user interface operatively associated with said controller, and with said controller confignred to:

optionally generating a warning signal prior to said first treatment waveform; then generating a warning signal during said first treatment waveform, and then optionally generating a warning signal during said second treatment waveform.

82. A system according to claim 81, wherein said warning signal is an auditory, visual, or tactile signal.

83. A system according to claim 81, wherein said defibrillator is an external defibrillator.

84. A system according to claim 79, wherein said controller is configured so that said first treatment waveform has an energy of from about 1 to 400 Joules.

85. A system according to claim 79, wherein said controller is configured so that said second treatment waveform has an energy of from about 100 to 400 Joules.

86. A system according to claim 79, wherein said controller is configured so that said first treatment waveform and said second treatment waveform are sequential.

87. A system according to claim 79, wherein said controller is configured so that said second treatment waveform immediately follows said first treatment waveform.

88. A system according to claim 79, wherein said controller is configured so that said first treatment waveform and said second treatment waveform are at least partially interleaved.

89. A system according to claim 79, wherein said signal analyzer determines the likelihood of pulseless electrical activity by determining a viability index associated with the viability of the heart.

90. A system according to claim 89, wherein said first treatment waveform is delivered when the viability index indicates a high likelihood of pulseless electrical activity.

91. A system according to claim 90, wherein the viability index is determined based on the duration for which the patient is in ventricular fibrillation.

92. A system according to claim 90, wherein the viability index is determined based on an analysis of the patient waveform during ventricular fibrillation.

93. A system according to claim 92, wherein the analysis of the patient waveform produces a power spectrum of the patient waveform.

94. A system according to claim 92, wherein the analysis of the patient waveform produces a scaling structure of the patient waveform.

95. A system according to claim 92, wherein the analysis of the patient waveform produces an amplitude and frequency of the patient waveform.

96. A system according to claim 92, wherein the analysis of the patient waveform produces a median frequency of the patient waveform.

97. A system according to claim 92, wherein the analysis of the patient waveform produces a centroid frequency of the patient waveform.

98. A system according to claim 92, wherein the analysis of the patient waveform produces a combination of at least two of a power spectrum, a scaling structure, an amplitude and frequency, a median frequency and a centroid frequency of the patient waveform.

99. A system according to claim 90, wherein the viability index is determined based on cardiac motion of the patient's heart.

100. A system according to claim 90, wherein the viability index is determined based on user input.

101. A system according to claim 90, wherein the viability index is determined based on physiological measurements indicative of blood flow.

102. A system according to claim 101, wherein the physiological measurements are electrical measurements.

103. A system according to claim 101, wherein the physiological measurements are physical measurements.

104. A system according to claim 101, wherein the physiological measurements are chemical measurements.

105. A system according to claim 101, wherein the physiological measurements are a combination of at least two of electrical measurements, physical measurements are chemical measurements.

106. A system for defibrillation of the heart of a patient afflicted with ventricular fibrillation, comprising:
   a detector for detecting electrical activity from the heart of said patient during ventricular fibrillation;
   a power supply;
   a controller operatively associated with said detector and said power supply, said controller configured for delivering a defibrillation sequence, said defibrillation sequence optionally comprising a first treatment waveform, said first treatment waveform insufficient to defibrillate said heart, and then delivering a second treatment waveform that defibrillates said heart and restores organized electrical activity in said heart;
   and wherein said first treatment waveform is delivered when a high likelihood of pulseless electrical activity after defibrillation is determined, and said first treatment waveform is not delivered when a low likelihood of pulseless electrical activity after defibrillation is determined.

107. A system according to claim 106, wherein the likelihood of pulseless electrical activity is determined manually after delivery of a defibrillation treatment waveform to said patient.

108. A system according to claim 106, wherein the likelihood of pulseless electrical activity is determined automatically after delivery of a defibrillation treatment waveform to said patient by a signal analyzer operatively associated with said controller.

109. A system according to claim 108, wherein the signal analyzer determines the likelihood of pulseless electrical activity by determining a viability index associated with the viability of the heart.

110. A system according to claim 109, wherein said first treatment waveform delivered if the viability index indicates that the viability of the heart is insufficient.

111. A system according to claim 110, wherein the viability index is determined based on the duration for which the patient is in ventricular fibrillation.

112. A system according to claim 110, wherein the viability index is determined based on an analysis of the patient waveform during ventricular fibrillation.

113. A system according to claim 112, wherein the analysis of the patient waveform produces a power spectrum of the patient waveform.

114. A system according to claim 112, wherein the analysis of the patient waveform produces a scaling structure of the patient waveform.

115. A system according to claim 112, wherein the analysis of the patient waveform produces an amplitude and frequency of the patient waveform.

116. A system according to claim 112, wherein the analysis of the patient waveform produces a median frequency of the patient waveform.

117. A system according to claim 112, wherein the analysis of the patient waveform produces a centroid frequency of the patient waveform.

118. A system according to claim 112, wherein the analysis of the patient waveform produces a combination of at least two of a power spectrum, a scaling structure, an amplitude and frequency, a median frequency and a centroid frequency of the patient waveform.

119. A system according to claim 110, wherein the viability index is determined based on cardiac motion of the patient's heart.

120. A system according to claim 110, wherein the viability index is determined based on user input.

121. A system according to claim 110, wherein the viability index is determined based on a physiological measurement indicative of blood flow.

122. A system according to claim 111, wherein the physiological measurement is an electrical measurement.

123. A system according to claim 111, wherein the physiological measurement is a physical measurement.

124. A system according to claim 111, wherein the physiological measurement is a chemical measurement.

125. A system according to claim 111, wherein the physiological measurement is a combination of at least two of an electrial measurement, physical measurement and chemical measurement.

126. A system according to claim 110, further comprising a user interface operatively associated with said controller, said user interface configured for reporting an indicia of the viability index to an operator so that the operator may optionally determine based on the viability index whether the first treatment waveform is to be delivered to the patient.

127. A system according to claim 110, wherein said first treatment waveform delivered to the patient is adjusted based on the viability index.

128. A method for the external defibrillation of the heart of a patient afflicted with ventricular fibrillation, comprising the steps of:
   externally administering to said patient a first treatment waveform, said first treatment waveform insufficient to defibrillate said heart; and
   externally administering to said subject a second treatment waveform that defibrillates said heart and restores organized electrical activity to said heart;
   wherein said first treatment waveform is administered when a high likelihood of pulseless electrical activity after defibrillation is determined, and said first treatment waveform is not administered when a low likelihood of pulseless electrical activity after defibrillation is determined.

129. A method according to claim 128, wherein the likelihood of pulseless electrical activity is determined manually after delivery of a defibrillation treatment waveform to said patient.

130. A method according to claim 128, wherein the likelihood of pulseless electrical activity is determined automatically after delivery of a defibrillation treatment waveform to said patient.

131. A method according to claim 130, wherein the likelihood of pulseless electrical activity is represented as a viability index associated with the viability of the heart, and wherein said first treatment waveform is delivered if the viability index indicates a high likelihood of pulseless electrical activity.

132. A method according to claim 131, wherein the viability index is determined based on the duration for which the patient is in ventricular fibrillation.

133. A method according to claim 131, wherein the viability index is determined based on an analysis of the patient waveform during ventricular fibrillation.

134. A method according to claim 133, wherein the analysis of the patient waveform produces a power spectrum of the patient waveform.

135. A method according to claim 133, wherein the analysis of the patient waveform produces a scaling structure of the patient waveform.

136. A method according to claim 133, wherein the analysis of the patient waveform produces an amplitude and frequency of the patient waveform.

137. A method according to claim 133, wherein the analysis of the patient waveform produces a median frequency of the patient waveform.

138. A method according to claim 133, wherein the analysis of the patient waveform produces a centroid frequency of the patient waveform.

139. A method according to claim 133, wherein the analysis of the patient waveform produces a combination of at least two of a power spectrum, a scaling structure, an amplitude and frequency, a median frequency and a centroid frequency of the patient waveform.

140. A method according to claim 131, wherein the viability index is determined based on cardiac motion of the patient's heart.

141. A method according to claim 131, wherein the viability index is determined based on user input.

142. A method according to claim 131, wherein the viability index is determined based on a physiological measurement indicative of blood flow.

143. A method according to claim 142, wherein the physiological measurement is an electrical measurement.

144. A method according to claim 142, wherein the physiological measurement is a physical measurement.

145. A method according to claim 142, wherein the physiological measurement is a chemical measurement.

146. A method according to claim 142, wherein the physiological measurement is a combination of at least two of an electrical measurement, physical measurement and chemical measurement.

147. A method according to claim 131, further comprising reporting an indicia of the viability index to an operator so that the operator may optionally determine based on the viability index whether the first treatment waveform is to be administered to the patient.

148. A method according to claim 131, said first treatment waveform delivered to the patient is adjusted based on the viability index.

* * * * *

UNITED STATES PATENT AND TRADEMARK OFFICE
CERTIFICATE OF CORRECTION

PATENT NO. : 6,760,621 B2
DATED : July 6, 2004
INVENTOR(S) : Woolcott et al.

It is certified that error appears in the above-identified patent and that said Letters Patent is hereby corrected as shown below:

Column 21,
Line 64, should read -- 39. A system according to claim 21, further comprising at --

Signed and Sealed this

Sixteenth Day of November, 2004

JON W. DUDAS
*Director of the United States Patent and Trademark Office*